United States Patent [19]
Peck et al.

[11] Patent Number: 6,001,647
[45] Date of Patent: *Dec. 14, 1999

[54] IN VITRO GROWTH OF FUNCTIONAL ISLETS OF LANGERHANS AND IN VIVO USES THEREOF

[75] Inventors: Ammon B. Peck; Janet G. Cornelius, both of Gainesville, Fla.

[73] Assignee: Ixion Biotechnology, Inc., Alachua, Fla.

[*] Notice: This patent is subject to a terminal disclaimer.

[21] Appl. No.: 08/547,746

[22] Filed: Oct. 25, 1995

Related U.S. Application Data

[63] Continuation-in-part of application No. 08/432,434, Apr. 28, 1995, abandoned, which is a continuation-in-part of application No. 08/234,071, Apr. 28, 1994, Pat. No. 5,834,308.

[51] Int. Cl.[6] ............................................. C12N 5/00
[52] U.S. Cl. ........................... 435/325; 435/383; 435/384; 435/392
[58] Field of Search ................................... 435/325, 383, 435/384, 392

[56] References Cited

U.S. PATENT DOCUMENTS

| | | |
|---|---|---|
| 4,439,521 | 3/1984 | Archer et al. . |
| 4,946,438 | 8/1990 | Reemtsma et al. . |
| 5,646,035 | 7/1997 | Coon et al. . |

FOREIGN PATENT DOCUMENTS

| | | |
|---|---|---|
| 0 363 125 | 2/1989 | European Pat. Off. . |
| WO 86/01530 | 3/1986 | WIPO . |
| WO 93/00441 | 1/1993 | WIPO . |
| WO 94/23572 | 10/1994 | WIPO . |

OTHER PUBLICATIONS

Yu et al. (1990) Tianjin Medical Journal 18(11):643–47.
Nielsen (1985) Acta Endocrinologica, Suppl. 266:7–39.
Otonkoski et al. (1994) Diabetes 43:1164–66.
Watanabe et al. (1994) PNAS USA 91:3589–92.
Altman et al. (1984) Trans. Am. Soc. Artif. Intern. Organs 30:382–386.
Hellerstrom et al. (1988) in The Pathology of the Endocrine Pancreas in Diabetes, P.J. Lefebvre and D.G. Pipeleers, eds., Springer–Verlag, Heidelberg, Germany, pp. 141–170.
Rosenberg et al. (1992) in Pancreatic Islet Cell Regeneration and Growth, A.I. Vinik, ed., Plenum Press, New York, pp. 95–109.
Beattie et al. (1994) J. Clin. Endocrin. Metabol. 78:1232–40.
Teitelman et al. (1993) Development 118:1031–39.
Menger et al. (1994) J. Clin. Invest. 93:2280–85.
Wegmann et al. (1993) J. Autoimmunity 6:517–27.
Otonkoski et al. (1994) Diabetes 43:947–53.
Gu et al. (1993) Development 118:33–46.
Bonner–Weir et al. (1993) Diabetes 42:1715–20.
Pictet et al. (1972) in Handbook of Physiology, R.L. Pictet et al., eds., Williams & Wilkins, Baltimore, MD, pp. 25–66.

Wang et al. (1987) Diabetes 36:535–538.
Kanaka–Gantenbein et al. (1995), Endocrinology, 138(7):3154–3162.
Nielson, Diabetes (1994), 43: No. 2, 7–39.
Peck et al., European Journal of Immunology (1973), 3:385–392.
Peck et al., Journal of Immunological Methods (1973), 3:147–164.
Pontesilli et al., Clin. exp. Immunol (1987), 70:84–93.
Rao et al., Cell Differentiation and Development (1990), 29(3):155–163 (1996).
Reddy et al., Diabetologia (1988), 31:322–328.
Shieh et al., Autoimmunity (1993), 15:123–135.
Signore et al., Diabetologia (1989), 32:282–289.
Takakai, In Vitro Cellular & Developmental Biology (1989), 25:No. 9, 763–769.
Teitelman, Tumor Biol. (1993), 14:167–173.
Vinik, Pancreatic Islet Cell Regeneration and Growth (1992), 1–5.
Wang et al., Diabetes (1987), 36:535–538.
Yu, et al., Tianjin Medical Journal, (1990), 18:No. 11, 643–47 (1990).
Kuo et al., Pancreas, (1992), 7(3):320–325.
Kuo et al., (Abstract), Clinical Research, (1990), 28(1):58A.
Anderson et al., Autoimmunity (1993), 15:113–122.
Baekkeskov et al., Nature, (1990), 347:151–156.
Baekkeskov et al., Nature (1982), 298:167–169.
Bendelac et al., The Journal of Immunology (1988), 141:2625–2628.
Bendelac et al., J. Exp Med. (1987) 166:823–832.
Brelje et al., Diabetes (1994), 43(2):263–273.
Gazdar et al., Proc. Natl. Acad. Sci. (1980), 77:No. 6,3519–3523.
Hamashima et al., Cellular, Mollecular and Genetic Approaches to Immunodiagnosis and Immunotherapy (1987), 219–226 (1987).
Hanafusa et al., Diabetes, (1988), 37:204–208.
Jarpe et al., Regional Immunology (1990/1991), 3:305–317.
Korsgren et al., Upsala J. Med. Sci. (1993), 98:No. 1, 39–50.
McEvoy et al., Endocrinology (1982), 111:No. 5, 1568–1575.
Miller et al., The Journal of Immunology (1988), 140(1):52–58.

Primary Examiner—Leon B. Lankford, Jr.
Attorney, Agent, or Firm—Swanson & Bratschun, L.L.C.

[57] ABSTRACT

The subject invention concerns new methods which make it possible, for the first time, to grow functional islets in in vitro cultures. The subject invention also concerns the use of the in vitro grown islet-like structures for implantation into a mammal for in vivo therapy of diabetes. The subject invention further concerns a process using the in vitro grown islet implants for growing an organ in vivo that has the same functional, morphological and histological characteristics as those observed in normal pancreatic tissue. The ability to grow these cells in vitro and organs in vivo opens up important new avenues for research and therapy relating to diabetes.

19 Claims, 11 Drawing Sheets

3-DIMENSIONAL IMAGING OF IN VITRO-INDUCED ISLET-LIKE STRUCTURES

IN VITRO GROWTH OF FUNCTIONAL ISLETS OF LANGERHANS AND IN VIVO USES THEREOF

This application is a continuation-in-part of copending U.S. application Ser. No. 08/432,434, filed Apr. 28, 1995, now abandoned, which is a continuation-in-part of copending U.S. application Ser. No. 08/234,071, filed Apr. 28, 1994, now U.S. Pat. No. 5,834,308.

BACKGROUND OF THE INVENTION

Diabetes is a major public health problem. As presented in the 1987 Report of The National Long-Range Plan to Combat Diabetes commissioned by the National Diabetes Advisory Board, six million persons in the United States are know to have diabetes, and an additional 5 million have the disease which has not yet been diagnosed. Each year, more than 500,000 new cases of diabetes are identified. In 1984, diabetes was directly causal in 35,000 American deaths and was a contributing factor in another 95,000.

Ocular complications of diabetes are the leading cause of new cases of legal blindness in people ages 20 to 74 in the United States. The risk for lower extremity amputation is 15 times greater in individuals with diabetes than in individuals without it. Kidney disease is a frequent and serious complication of diabetes. Approximately 30 percent of all new patients in the United States being treated for end-stage renal disease have diabetes. Individuals with diabetes are also at increased risk for periodontal disease. Periodontal infections advance rapidly and lead not only to loss of teeth but also to compromised metabolic function. Women with diabetes risk serious complications of pregnancy. Current statistics suggest that the mortality rates for infants of mothers with diabetes is approximately 7 percent.

Clearly, the economic burden of diabetes is enormous. Each year, patients with diabetes or its complications spend 24 million patient-days in hospitals. A conservative estimate of total annual costs attributable to diabetes is at least $24 billion (American Diabetes Association est., 1988); however, the full economic impact of this disease is even greater because additional medical expenses often are attributed to the specific complications of diabetes rather than to diabetes itself.

Diabetes is a chronic, complex metabolic disease that results in the inability of the body to properly maintain and use carbohydrates, fats, and proteins. It results from the interaction of various hereditary and environmental factors and is characterized by high blood glucose levels caused by a deficiency in insulin production or an impairment of its utilization. Most cases of diabetes fill into two clinical types: Type I, or juvenile-onset, and Type II, or adult-onset. Type I diabetes is often referred to as Insulin Dependent Diabetes, or IDD. Each type has a different prognosis, treatment, and cause.

Approximately 5 to 10 percent of diabetes patients have IDD. IDD is characterized by a partial or complete inability to produce insulin usually due to destruction of the insulin-producing $\beta$ cells of the pancreatic islets of Langerhans. Patients with IDD would die without daily insulin injections to control their disease.

Few advancements in resolving the pathogenesis of diabetes were made until the mid-1970s when evidence began to accumulate to suggest that Type I IDD had an autoimmune etiopathogenesis. It is now generally accepted that IDD results from a progressive autoimmune response which selectively destroys the insulin-producing $\beta$ cells of the pancreatic Islets of Langerhans in individuals who are genetically predisposed. Autoimmunity to the $\beta$ cell in IDD involves both humoral (Baekkeskov et al., 1982; Baekkeskov et al., 1990; Reddy et al. 1988; Pontesilli et al., 1987) and cell-mediated (Reddy et al. 1988, supra; Pontesilli et al., 1987, supra; Wang et al., 1987) immune mechanisms. Humoral immunity is characterized by the appearance of autoantibodies to $\beta$ cell membranes (anti-69 kD and islet-cell surface autoantibodies), $\beta$ cell contents (anti-carboxypeptidase $A_1$, anti-64 kD and/or anti-GAD autoantibody), and/or $\beta$ cell secretory products (anti-insulin). While serum does not transfer IDD, anti-$\beta$ cell autoantibody occurs at a very early age, raising the question of an environmental trigger, possibly involving antigenic mimicry. The presence of cell-mediated immunological reactivity in the natural course of IDD is evidenced by an inflammatory lesion within the pancreatic islets, termed insulitis. Insulitis, in which inflammatory/immune cell infiltrates are clearly visible by histology, has been shown to be comprised of numerous cell types, including T and B lymphocytes, monocytes and natural killer cells (Signore et al., 1989; Jarpe et al. 1991). Adoptive transfer experiments using the NOD (non-obese diabetic) mouse as a model of human IDD have firmly established a primary role for auto-aggressive T lymphocytes in the pathogenesis of IDD (Bendelac, et al., 1987; Miller et al., 1988; Hanafusa et al., 1988; Bendelac et al., 1988). Unfortunately, the mechanisms underlying destruction of the pancreatic $\beta$ cells remain unknown.

Recent efforts to culture pancreatic cells, including efforts reported in the following publications, have focused on cultures of differentiated or partially differentiated cells which in culture have grown in monolayers or as aggregates. By contrast to these reports, the instant invention discloses a method and a structure wherein an islet-like structure is produced which has a morphology and a degree of cellular organization much more akin to a normal islet produced in vivo through neogenesis.

Gazdar, et al., (1980) disclosed a continuous, clonal, insulin- and somatostatin-secreting cell line established from a transplantable rat islet cell tumor. However, the cells disclosed were tumorigenic and were not pluripotent.

Brothers, A. J. (WO 93/00441, 1993) disclosed hormone-secreting cells, including pancreatic cells, maintained in long-term culture. However, the cells cultured are differentiated, as opposed to pluripotent stem cells, which are selected at an early stage for their hormone secreting phenotype, as opposed to their capacity to regenerate a pancreas-like structure.

Korsgren, et al., disclosed an in vitro screen of compounds for their potential to induce differentiation of fetal porcine pancreatic cells. The instant invention does not depend on the use of fetal tissue.

Nielsen, J. H., (WO 86/01530, 1986) disclosed a method for proliferation of wholly or partially differentiated beta cells. However, this disclosure depended on fetal tissue as a source of the islet cells grown in culture.

McEvoy et al., (1982) disclosed a method for tissue culture of fetal rat islets and compared the effect of serum on the defined medium maintenance, growth and differentiation of A, B, and D cells. Once again, the source of islet cells is fetal tissue.

Zayas et al, (EP 0 363 125, 1990), disclosed a process for proliferation of pancreatic endocrine cells. The process depends on the use of fetal pancreatic tissue, and a synthetic structure, including collagen must be prepared to embed these cells for implantation. The thus produced aggregates of cultured cells upon implantation require 60–90 days before having any effect on blood glucose levels, and require 110–120 days before euglycemia is approached. By contrast, the instant invention provides in vitro grown islet-like structures which do not require collagen or other synthetic means for retention of their organization, and which, upon implantation, provide much more rapid effects on the glycemic state of the recipient.

Coon et al., (WO 94/23572, 1994) disclosed a method for producing an expanded, non-transformed cell culture of pancreatic cells. Aggregated cultured cells are then embedded in a collagen matrix for implantation, with the attendant shortcomings noted for the Zayas et al., supra structures and the distinctions noted with the structure produced according to the instant invention.

Despite the foregoing reports, the instant invention, wherein functional islet-like structures containing cells which express insulin, glucagon and/or somatostatin which can be implanted into clinically diabetic mammals which subsequently remain healthy (after elimination of insulin treatment), is surprising. This is because conventional and immunofluorescent histology of the pancreatic islets of Langerhans (Lacey et al., 1957; Baum et al., 1962; Dubois, 1975; Pelletier et al., 1975; Larsson et al., 1975), together with recent three dimensional imaging Brelje et al., 1989), have revealed a remarkable architecture and cellular organization of pancreatic islets ideal for rapid, yet finely controlled, responses to changes in blood glucose levels. It could not be predicted that such a structure could be produced in vitro, particularly when one considers that during embryogenesis, islet development within the pancreas appears to be initiated from undifferentiated precursor cells associated primarily with the pancreatic ductal epithelium (Pictet et al., 1972) i.e. non-islet cells. The ductal epithelium rapidly proliferates, then subsequently differentiates into the various islet-associated cell populations (Hellerstrom, 1984; Weir et al., 1990; Teitelman et al., 1993; Beattie et al., 1994). The resulting islets are organized into spheroid structures in which insulin-producing β cells form a core surrounded by a mantle of non-β cells. For the most part, glucagon-producing α cells (if the islet is derived from the dorsal lobe) or alternatively, pancreatic peptide-producing, PP cells (if the islet is derived from the ventral lobe), reside within the outer cortex (Brelje et al., supra, 1989; Weir et al., supra, 1990). Somatostatin-producing δ cells, which are dendritic in nature, reside within the inner cortex and extend pseudopodia to innervate the α (or PP) cells and the β cells. These spheroid islet structures tend to bud from the ductal epithelium and move short distances into the surrounding exocrine tissue. Angiogenesis-induced vascularization results in direct arteriolar blood flow to mature islets (Bonner-Weir et al., 1982; Teitelman et al., 1988; Menger et al., 1994). Since blood glucose can stimulate β cell proliferation, vascularization may act to increase further the numbers of β cells. Similarly, neurogenesis leads to the innervation of the islets with sympathetic, parasympathetic and peptidergic neurons (Weir et al., supra, 1990). That we have been able to produce functional islet-like structures in vitro which can then be implanted to produce pancreas-like structures, is therefore quite remarkable.

Unfortunately, the cellular organization of the islet can be destroyed in diseases such as type I, insulin dependent diabetes (IDD), in which a progressive humoral and cell-mediated autoimmune response results in specific destruction of the insulin-producing β cells (Eisenbarth, 1986; Leiter et al., 1987). Because the β cell is considered to be, for the most part, a differentiated end-stage cell, it is believed that the body has limited capacity to generate new β cells, thus necessitating regular life-long insulin therapy once the β cell mass is destroyed. However, in experimental animals, the β-cell mass has been shown to increase and decrease in order to maintain euglycemia (Bonner-Weir et al., 1994). This plasticity can occur through two pathways of islet growth: first, by neogenesis, or growth of new islets by differentiation of pancreatic ductal epithelium, and second, by hypertrophy, or expansion through replication of preexisting β cells. During embryogenesis, the β-cell mass initially expands from differentiation of new cells, but by the late fetal stages the differentiated β cells replicate. Replication, then, is likely to be the principal means of expansion after birth, but the capacity to replicate appears to diminish with age. Adult islet cells have been shown to replicate by responding to stimuli known to initiate neonatal islet cell growth, e.g., glucose, growth hormone, and several peptide growth factors (Swenne, 1992; Hellerstrom et al., 1988; Bonner-Weir et al., 1989, Marynissen et al., 1983; Neilsen et al., 1992; Brelje et al., 1993). These observations suggest that the low level of β-cell growth in the adult can accommodate functional demands. For example, during pregnancy or chronic obesity, βcell mass increases significantly yet is reversible since, following termination of pregnancy or after weight loss, an increased β cell death via apoptosis quickly reduces β cell mass.

It is generally accepted that all pancreatic endocrine cell types differentiate from the same ductal epithelium (Pictet et al., 1972, supra; Hellerstrom, 1984, supra; Weir et al., 1990, supra; Teitelman et al., 1993, supra), but whether they are derived from a common stem/precursor cell is uncertain. In normal adult pancreas, approximately 0.01% of the cells within the ductal epithelium will express islet cell hormones and can be stimulated to undergo morphogenic changes to form new islets, reminiscent of neogenesis. This neogenesis has been irduced experimentally by dietary treatment with soybean trypsin inhibitors (Weaver et al., 1985), high levels of interferon-γ (Gu et al., 1993), partial pancreatectomy (Bonner-Weir et al., 1993), wrapping of the head of the pancreas in cellophane (Rosenberg et al., 1992), specific growth factors (Otonkoski et al., 1994) and the onset of clinical IDD. Recently, attention has focused on the Reg gene (Watanabe et al., 1994, Otonkoski et al., 1994), identified in a subtracted cDNA library of regenerating rat islets, as a controlling element in the neogenesis of islet β cells. Up-regulation of the Reg gene (e.g., by hepatocyte growth factor/scatter factor) induces β cell proliferation resulting in increased mass, while down-regulation of the Reg gene (e.g., by nicotinamide) induces differentiation of the 'pre-β' cells to mature cells. Thus, a population of precursor/stem cells remain in the adult pancreatic ducts and differentiation of this population can be evoked in vivo in response to specific stimuli. This action may actually occur continuously at low levels.

Although intensive efforts have been made to reproduce islet neogenesis in vitro, minimal success has been achieved. We now describe, for the first time, conditions which permit the growth and expansion of mammalian-derived islet-producing stem cells (IPSCs) in culture, as well as their differentiation to islet-like structures.

Numerous strategies (e.g., bone marrow replacement, immunosuppressive drugs and autoantigen immunizations) have been investigated as possible means to arrest the immunological attack against the pancreatic β cells. However, for these approaches to be effective, individuals who will eventually develop clinical disease must be identified. Most often, patients are identified too late for effective intervention therapy since the immunological attack has progressed to a point where a large percentage of the β cells have already been destroyed. Because the β cell is thought to be an end-stage differentiated cell, it was previously believed that the body has little capacity to regenerate new β cells, thus necessitating regular life-long insulin therapy. Recently, one approach to overcome this problem has been islet cell transplantation. Islet cell transplantation has the disadvantage that the islets are allogeneic which, in turn, can invoke an allo-immune response. Thus, there would be major advantages to growing Islets of Langerhans containing functional β cells directly from IDD patients.

BRIEF SUMMARY OF THE INVENTION

The subject invention concerns the discovery that functional islets containing insulin-producing β cells, as well as other islet cell types, can be grown in long-term cultures from pluripotent stem cells, which give rise to islet producing stem cells, IPSCs.

The novel methods of the subject invention take advantage of the discovery that IPSCs exist even in the pancreas of adult individuals. The cells can be cultured in a minimal, high amino acid nutrient medium that is supplemented with normal serum which is preferably derived from the same mammalian species which serves as the origin of the islet cells (homologous serum). Several discrete phases of cell growth result in selection of IPSCs and subsequent progeny which are then induced to differentiate and form islet-like structures which are distinguishable from pseudo-islet or pseudo-pancreatic tissue of the prior art. In a first phase, primary culture of cells from a pancreas are placed in a low serum, low glucose, high amino-acid basal medium. This culture is then left undisturbed for s veral weeks to permit establishment of stromal cells and to allow the vast majority of differentiated cells to die. Once this stromal cell layer is mature, cell differentiation can be initiated by re-feeding the cell culture with the high amino acid medium supplemented with homologous normal serum plus glucose. After an additional period of growth, functional islets containing cells which produce insulin, glucagon, somatostatin and other endocrine hormones can then be recovered using standard techniques.

It was not previously known or suspected that pancreatic-derived non-islet cells (ductal derived cells) could be used to grow new islet-like structures, including β cells, in culture. The fortuitous discovery of culture techniques for growing islet-like tissue in vitro eliminates what had previously been a substantial and longstanding barrier to diabetes research. The novel methods and materials described herein enable a better understanding of the mechanisms of diabetes. Furthermore, the ability to produce islet-like structures from IPSCs in culture now makes certain therapies for diabetes possible for the first time. For example, in accordance with the subject invention, new cultured islets from diabetic individuals can be implanted in a patient as a way to control or eliminate the patient's need for insulin therapy because the cultured islets and/or islet cells are able to produce insulin in vivo. Thus, the subject invention also concerns the use of the in vitro grown islets of the subject invention for implantation into a mammalian species for in vivo treatment of IDD.

The subject invention also greatly facilitates genetic engineering of islet cells to resist subsequent immunological destruction. For example, the cultured islet cells can be transformed to express a protein or peptide which will inhibit or prevent the destructive immune process. Other useful proteins or peptides may be expressed. In addition, expression of specific autoantigens, such as GAD, 64 kD islet cell surface antigens (see Payton et al., 1995), or any other markers identified on the differentiated pancreatic cells, can be eliminated by standard gene knock-out or selection procedures to produce differentiated pancreatic cells which are not or are less susceptible to auto-immune attack. Methods for producing such mutant or knock out cell lines are well known in the art and include, for example, homologous recombination methods disclosed in U.S. Pat. Nos. 5,286,632; 5,320,962; 5,342,761; and in WO 90/11354; WO 92/03917; WO 93/04169; WO 95/17911, all of which are herein incorporated by reference for this purpose. In addition, a universal donor cell is produced by preparing a stem cell modified so as not to express human leukocyte antigen (HLA) markers as the cell differentiates into a pancreas-like structure (see especially WO 95/17911, supra).

Thus, the ability to grow functioning islets in vitro from the pancreatic cells of an individual represents a major technical breakthrough and facilitates the use of new strategies for treating and studying IDD. The discovery that pluripotent stem cells exist in adult pancreas circumvents (without excluding) the need to use fetal tissue as a source of cells.

The subject invention also concerns the islet cells produced in vitro according to the methods described herein. These cells are produced from a mammalian pancreatic cell suspension cultured in vitro and give rise to functional islet cells and islet-like tissue structures.

The subject invention further concerns the in vitro growth, propagation and differentiation of a pancreatic stem cell, i.e., a progenitor cell or cells that give rise to the formation of all of the different types of cells and tissue that make up a normal pancreas. Moreover, the subject invention concerns the in vivo use of in vitro grown pancreatic stem cells to produce pancreas-like structures or an "ecto-pancreas" organ that exhibits functional, morphological and histological characteristics similar to those observed in a normal pancreas. Thus, the ability to produce a functional "ecto-pancreas" in vivo from in vitro grown pancreatic cells can be used to treat, reverse or cure a wide variety of pancreatic diseases that are known to result in or from damage or destruction of the pancreas.

BRIEF SUMMARY OF THE FIGURES

In FIG. 6B, the structure has disintegrated, and most of the cells have died, but in FIG. 6C a new structure develops. In FIG. 6D, several new structures have formed. This series of serial passage steps can be repeated a number of times until the IPSCs become depleted. In this event as the structure disintegrates, as in FIG. 6E, instead of new structures being formed, the differentiated cells multiply, as shown in FIG. 6F. It is this type of proliferated differentiated cell that is thought to have been produced by workers such as Coon et al. (see WO 94/23572, supra).

ABBREVIATIONS AND DEFINITIONS

IPSCs are Islet Producing Stem Cells. IPSCs are a small population of cells derived from ductal epithelial cells (i.e., these cells are pancreas-derived but are not differentiated islet cells) discovered in fetal or adult pancreas which, according to this invention, have the capacity of giving rise to islet-like structures in vitro. When ductal epithelial cells in combination with the islet-like structures are implanted in vivo, a pancreas-like structure is formed. When the pancreas-like structure and ductal epithelial cells are implanted in a location other than the natural pancreatic location in vivo, the pancreas-like structure is referred to as an ecto-pancreas.

Pluripotent pancreas stem cells are cells discovered in the pancreas which give rise to IPSCs.

Mature islet cells are differentiated cells which arise from IPSCs and which produce pancreatic hormones.

Figure 3:
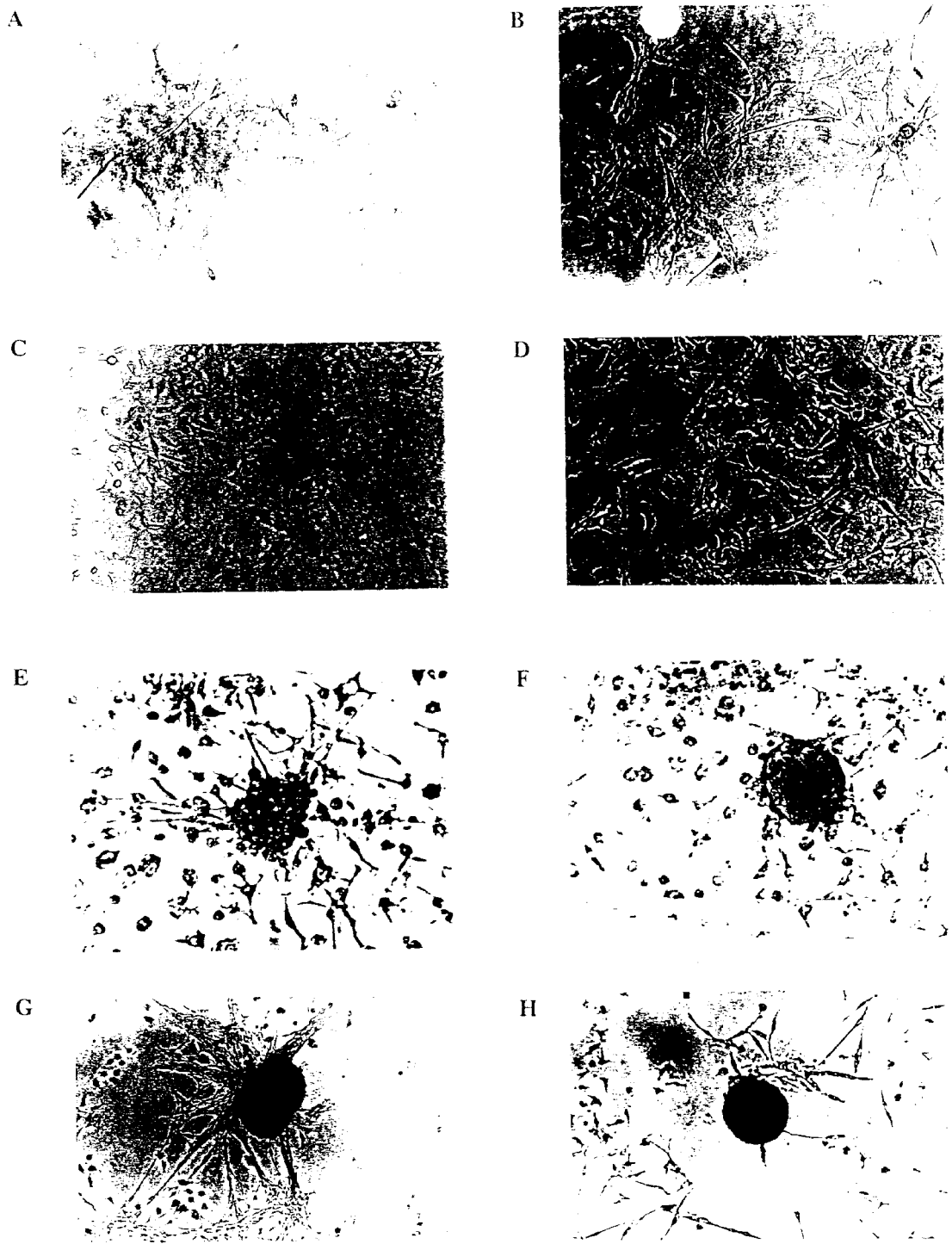
FIGS. 3A through 3H shows sequential stages in the development of an islet-like structure in vitro from 3A, which shows a few cells after several weeks in culture, which have survived and which begin to "bud" (FIG. 3B, dark structure in top right-hand of field), and divide (FIG. 3C several locations in field), and to form highly organized structures (FIGS. 3D–3H) under the culture conditions described herein.
Figure 4A:
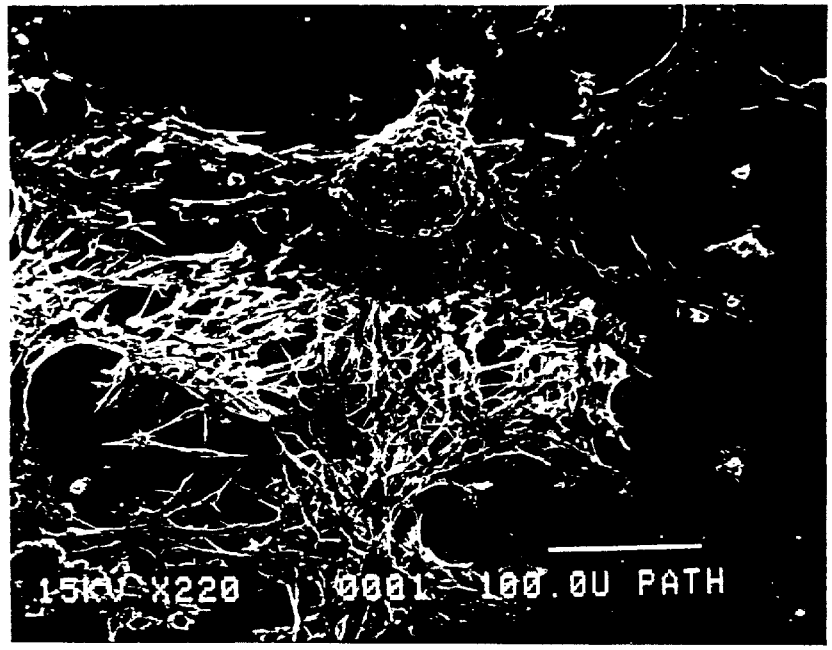
FIGS. 4A and 4B show photomicrographs of the structures shown in FIGS. 3G–3H, showing the highly organized morphology thereof.
Figure 4B:
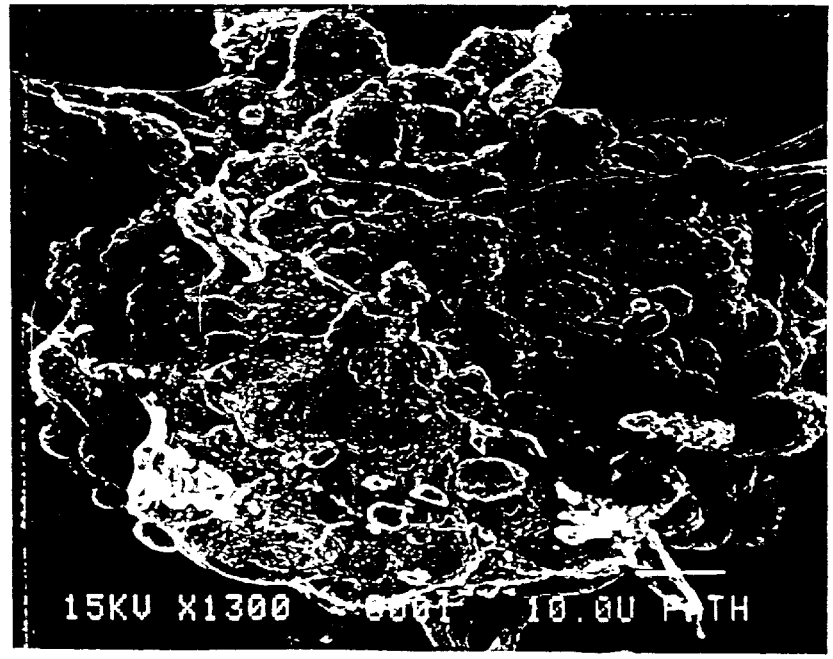
Figure 5:
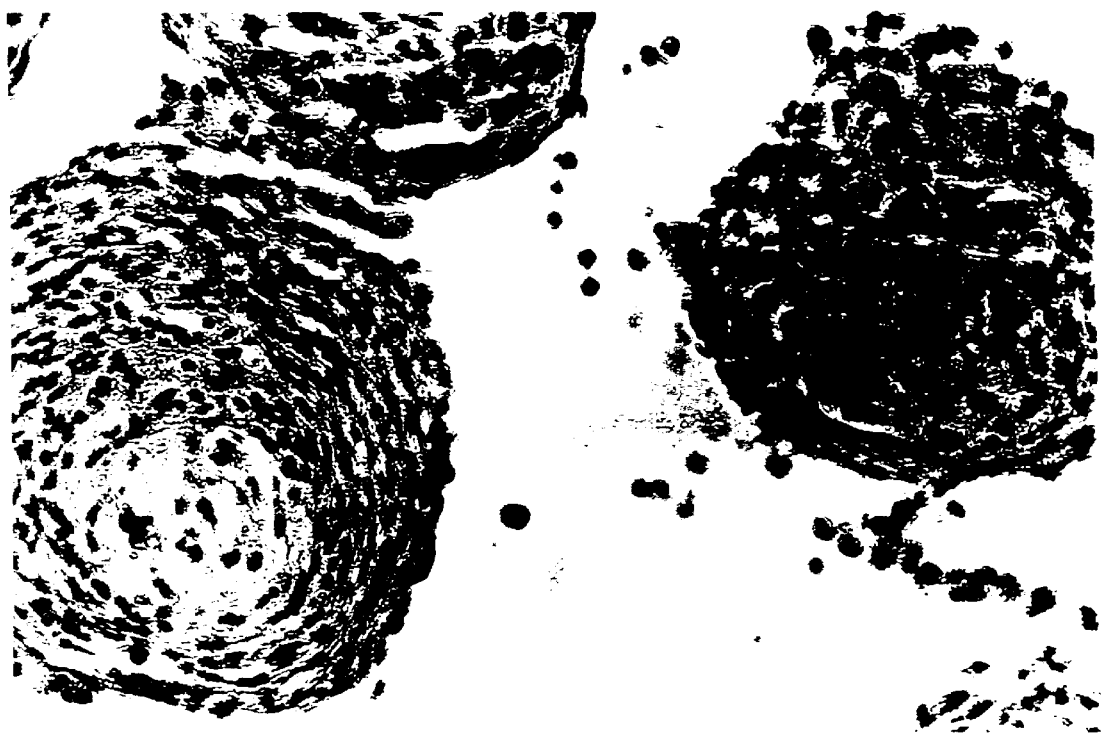
FIG. 5 shows H/E staining of an islet-like structure cross-sections showing the highly organized morphology of the structure with β-cells in the center and glucagon-producing cells at the periphery.

Islet-like structures, or young-islets, are highly-organized structures of cells which we have discovered arise in culture from IPSCs (see FIG. 3H, FIGS. 4A and 4B, and cross-section shown in FIG. 5). The structures "bud" from foci formed by individual IPSCs after most of the cells, which are not IPSCs, which are placed into culture from dissociated pancreatic tissue, have died. Upon implantation of the islet-like structure, final differentiation occurs to produce fully mature islet cells.

DETAILED DESCRIPTION OF THE INVENTION

According to the subject invention, functional Islets of Langerhans can for the first time be grown in in vitro cultures. The techniques of the subject invention result in cell cultures which can produce insulin, glucagon, somatostatin or other endocrine hormones. Other useful proteins may also be produced by, for example, transforming the islet cell with DNA which encodes proteins of interest. The ability to grow these functional cell cultures enables those skilled in the art to carry out procedures which were not previously possible. In the following disclosure, the term islet-like structure should be read as being interchangeable with the term "yonng-islets", because these in vitro produced structures have most of the attributes of islets produced in vivo during normal neogenesis. The immature nature of these structures permits implantation in vivo with rapid final differentiation and vascularization ensuing to provide a functioning replacement to damaged or otherwise compromised islets in recipients such as diabetic or prediabetic mammals, in need of such treatment.

The method of the subject invention involves making suspensions of cells, including stem cells, from the pancreas of a mammal. Preferably, the stem cells would be from the pancreas of a prediabetic mammal. However, it is also contemplated that islet producing stem cells, IPSCs, from mammals already showing clinical signs of diabetes, can be utilized with the subject invention. The cell suspensions are prepared using standard techniques. The cell suspension is then cultured in a nutrient medium that facilitates the growth of the IPSCs, while at the same time severely compromising the sustained growth of the differentiated or mature cells other than IPSCs. In a preferred embodiment, the nutrient medium is one which has a high concentration of amino acids. One such medium is known as Click's EHAA medium and is well known and readily available to those skilled in the art (Peck and Bach, 1973, herein incorporated by reference for this purpose). Other equivalent nutrient media could be prepared and utilized by those skilled in the art. What is required for such media is that they have little or no glucose (less than about 1 mM) and low serum (less than about 0.5%). The high amino acid concentrations are preferably of amino acids known to be essential for the cells of the species being cultured, and provide a carbon source for the cultured cells. In addition, at least one rudimentary lipid precursor, preferably pyruvate, is provided. These conditions are so stressful to most differentiated cell types that they do not survive. Surprisingly, however, upon extended culture of cells from pancreatic tissue without re-feeding (about 3 weeks) IPSCs do survive and after extended culture, begin to proliferate. Subsequent culture phases employ media supplemented with normal serum from the same species of mammal from which the islet cells originate. Thus, in the case of mouse islets, the medium is supplemented with normal mouse serum, whereas in the case of human islet cells the medium is supplemented with normal human serum. The preparation of normal serum is well known to those skilled in the art. The concentration of normal serum used with the cell culture method of the subject invention can range from about 0.5% to about 10%, but for mice is preferably about 1%. For human serum, a higher concentration is preferred, for example, about 5%.

The cell suspension prepared in the nutrient medium supplemented with normal serum and about 2.5–10 mM glucose is then incubated under conditions that facilitate cell growth, preferably at about 35–40° C. and, preferably, in an atmosphere of about 5% $CO_2$. This incubation period is, thus, carried out utilizing standard procedures well known to those skilled in the art. During this time stromal or ductal epithelial cells proliferate and establish a monolayer which will ultimately give rise to islet-like structures. The initiation of cellular differentiation can be brought about by re-feeding the cultures with Click's EHAA or like medium supplemented with normal serum as discussed above. Rapid re-feeding was found to induce extensive islet foci and islet-like structure formation with considerable cell differentiation. We have found that cellular differentiation is further enhanced by inclusion of relatively high concentrations of glucose (about 10–25 mM and preferably 16.7 mM) in the re-feed medium. In addition, it is contemplated that any of a number of other biological factors, including but not limited to factors which up-regulate the Reg gene, such as hepatocyte growth/scatter factor, and other cellular growth factors, such as insulin-like-growth factor, epidermal growth factor, keratinocyte growth factor, fibroblast growth factor, nicotinamide, and other factors which modulate cellular growth and differentiation can be added to the cultures to optimize and control growth and differentiation of the IPSCs. By employing any of these various factors, or combinations thereof, at different stages, at different seeding densities and at different times from seeding in the course of IPSC differentiation, IPSC cultures are optimized. In addition, factors produced by the IPSC cultures in the course of differentiation which augment growth can be isolated, sequenced, cloned, produced in mass quantities, and added to IPSC cultures to facilitate growth and differentiation of those cultures. The relevant factors are identified by concentrating IPSC culture supernates from early, intermediate and late stages of differentiation and testing for the ability of these concentrates to augment IPSC growth and differentiation. Positive effects are correlated with molecular constituents in the concentrates by two-dimensional gel electrophoresis of positive and negative supernates, purification and N-terminal sequencing of spots present only in the positive concentrates and subsequent cloning and expression of the genes encoding these factors.

Upon histological examination of the cells in the islet-like structures, at least three distinct cell types were identifiable and appeared similar to islet cells prepared from islets of control mice. The time required for cell differentiation to occur within these foci decreased as the frequency of re-feeding was increased.

We have been able to propagate and expand isletproducing cultures through the serial transfer of islet-derived stromal cells plus islet foci to new culture flasks. This facilitates generating sufficient numbers of islets as required for use in methods described herein, for example, for reversing the metabolic problems of IDD.

In order to determine whether the islet-like structures and/or islet cells produced in vitro according to the subject invention could reverse IDD, the islet-like structures were implanted into NOD mice. Mice that received the islet implants exhibited a reversal of insulin-dependent diabetes, whereas untreated NOD mice showed signs of clinical disease. In addition, no autoinimune pathogenesis was observed during the duration of the implants. Thus, islet implants of the subject invention can be used in vivo to treat diabetes in mammals, including humans.

In a preferred embodiment of the subject invention, the progression of diabetes can be slowed or halted by re-implantation of autologous islets engineered to be resistant to specific factors involved in the immunological attack. For example, the islets can be engineered so that they are resistant to cytotoxic T cells (see, for example, Durinovic et al., 1994, identifying islet specific T-cells and T-cell receptor sequences which are similar to insulitis-inducing T-cells of diabetic mice; Elias and Cohen, 1994, identifying peptide sequences useful in diabetes therapy in NOD mice by turning-off production of specific diabetogenic T-cell clones; Conrad et al., 1994, describing a membrane-bound, islet cells superantigen which triggers proliferation of islet infiltrating T-cells; Santamaria et al., 1994, describing the requirement of co-expression of B7-1 and TNFA for diabetes and islet cell destruction; any of these antigens may be eliminated according to known methods to improve the resistance of the implanted islets against immunologic attack). The availability of long-term cultures of whole islets can also be used in investigations into the pathogenesis of IDD, including the cellular recognition of β cells, the mode of islet infiltration, and the immune mechanisms of β cell destruction. Furthermore, this technology facilitates islet transplantation, autologous islet replacement, and development of artificial islets. The growth of these cells and islet-like structures according to the procedures of the subject invention has great utility in teaching students and in increasing the understanding of important aspects relating to cell differentiation and function.

In a further embodiment of the subject invention, pluripotent pancreatic stem cells, which give rise to ISPCs, have been grown in vitro from pancreas cells isolated from a mammal. A surprising discovery using these in vitro grown cells in conjunction with the methods of the subject invention, was the ability lo grow and produce, in vivo, an organ that exhibited functional, morphological and histological features and characteristics similar to a normal pancreas, including cell differentiation, to form endocrine and exocrine tissues. The ecto-pancreas, (a pancreas-like organ situated at an abnormal site within the body cavity), produced in vivo according to the subject invention, represents a major scientific discovery and provides a novel means for studying, treating, reversing or curing a number of pancreas-associated pathogenic conditions including but not limited to pancreatitis, pancreatic cancer and IDD. This is accomplished by removal of the diseased tissue and implantation of the islet-like structures produced according to this invention. In addition, the islet-like structures can be implanted into the natural pancreatic site.

Because this invention provides a method for culturing pancreatic stem cells and production of young islets in vitro, study of the growth and differentiation of this cell-type is now possible. Accordingly, all of the known methods of cell culture, purification, isolation and analysis can be brought to bear on the significant questions regarding how many types of cells are involved in pancreatic cell differentiation. These methods include, but are not limited to, fluorescence activated cell sorting (FACS), magnetic bead usage (as in, for example, the use of the commercially available DYNA BEADS which are specifically adapted for this purpose), use of magnetically stabilized fluidized beds (MSFB, see U.S. Pat. No. 5,409,813), and any of a number of other methods known in the art. The pathway for this process is now amenable to dissection. Identification of markers (including cell-surface, intracellular, protein or mRNA), specific to every stage of this process, are also now readily identifiable through application of standard techniques including, but not limited to: production of antibodies, including monoclonal antibodies, to cells, cell surface markers, and cellular components which differ throughout the process of pancreatic stem cell maturation; production of T-lymphocytes which specifically respond to antigens expressed by the pancreatic cells at different stages in the maturation and differentiation process (see for example Wegmann et al., 1993); identification and elimination of cell surface markers recognized by T-cells and which, therefore, result in differentiated β-cell destruction if present (see references above); identification of factors significant in bringing about the different stages of maturation and the different factors produced by the differentiating cells; subtractive hybridization of nucleic acids isolated from cells at different stages in the maturation process, enabling pinpointing of gene products significant to each aspect of the cellular differentiation; differentiated display PCR (see Liang et al., 1992); arbitrarily primed PCR (see Welsh et al., 1992); representational difference analysis PCR (RDA-PCR) (see Lisitsyn, 1993); encapsulation of single pancreatic progenitor cells or populations thereof for implantation in appropriate host organisms, thereby providing advantages that such methods have demonstrated in implantation of other types of progenitor or engineered cells (see Altman et al., 1994); genetic engineering of the pancreatic progenitor cells to produce cells less susceptible to autoimmune attack, such as by knock-out of autoantigen genes, or insertion of resistanci enhancing genes; other genes which may be inserted into the IPSCs include those which provide altered cellular surface antigens or which provide different biochemical properties to the internal milieu of the cells; these include genes which express enzymes which increase or decrease the sensitivity of the cells to glucose or genes which increase or decrease the responsiveness of the cells to growth factors; in addition, genes which increase or decrease the production of insulin, glucagon or somatostatin may also be introduced; examples of how these types of modifications can be introduced into the IPSCs include electroporation, virus vectors, transfection or any of a number of other methods well known in the art (see for example WO 95/17911; WO 93/04169; WO 92/03917; WO 90/11354; U.S. Pat. No. 5,286,632; WO 93/22443; WO 94/12650; or wo 93/09222; all of which are incorporated by reference for this purpose); production of universal donor (knock-out) cells which, for example, have deleted or otherwise modified human leukocyte antigens (see WO 95/17911, supra). Because this process does not depend on the use of fetal tissue, it is possible to remove pancreatic tissue from a mammal suffering from IDD or at risk of suffering from IDD, grow an islet-like structure in vitro and re-implant that structure into the individual to produce physiologically relevant amounts of insulin in response to fluctuations in blood glucose.

In view of the foregoing disclosure and the exemplary support which follows, it should be recognized that the scope of the appended clai ns extends to the various embodiments and aspects of this invention which those skilled in the art will recognize are enabled by this significant invention.

It will also be recognized that data presented herein reveal that in vitro neogenesis of islets from isolated pluripotent stem/progeritor cells is possible, but involves several distinct phases of growth, including: 1) Establishment of a stromal, or "nurse", cell monolayer of ductal epithelial cells which permits the generation of IPSCs. 2) Induction of stem/progenitor cell proliferation with specific culture conditions which promote cyclical regeneration of IPSCs and also prevent premature differentiation of the IPSC. 3) Expansion and differentiation of the α, β and δ cells. This step is dictated by the culture environment, as differences in culture nutrients and growth factors result in islets containing different percentages of the various islet cell types. Identification of in vitro conditions which induce the β cell to its final maturation stage, i.e., formation of insulin-containing granules and glucose responsiveness can also now be achieved. A factor present in vivo which achieves this final differentiation is identified by addition of cellular extracts or growth factors to the IPSC cultures.

We have maintained primary IPSC cultures for up to 10 months and secondary cultures an additional 14–16 months each capable of expansion and differentiation to form islet-like structures. While the ability to grow functioning islets from prediabetic adults represents a major technical breakthrough and focuses attention on possible new strategies for attaining a cure for IDD, perhaps the most important aspect of this work is the demonstration that pluripotent stem/progenitor cells, which can give rise to IPSCs and pancreas-like structures when implanted, exist in the islets of both normal and (pre)diabetic adults. This finding will eliminate the need to use either fetal, allogeneic or xenogeneic tissue for transplantation of β cells into IDD patients; to develop novel strategies to reverse hypoglycemia in vivo; study immunological responses to newly implanted islets; and/or create islets resistant to immunological attack.

It is tempting to speculate, based on the data presented herein, that the well-documented period of remission in type I IDD patients following onset of disease might actually represent a time when stem cell growtt. is induced, only to be subsequently overwhelmed by the on-going autoimmune reaction. Since re-implantation of autologous islets is thought to require cells engineered to be resistant to the immunological attack, identification and culture of islet stem cells as disclosed herein is essential for the genetic engineering efforts described above.

Surprisingly, the in vitro-generated islet implants of this invention showed no signs of immunological attack over the time period studied here. It is possible that the autoantigen(s) are not expressed on cultured cells, cr that the autoantigen(s) cannot be presented since culture dilutes out the macrophages, or such implants may induce peripheral tolerance. The availability of long-term cultures of whole islets facilitates investigations into the pathogenesis of IDD, including the cellular recognition of β cells, the mode of islet infiltration, and the immune mechanisms of β cell destruction. Furthermore, this technology facilitates islet transplantation, autologous islet replacement, development of artificial islets and reduces the need for insulin therapy.

Accordingly, this invention provides a method for the in vitro growth of islet producing stem cells, IPSCs, to produce an islet-like structure. The method comprises culturing pancreatic cells from a mammalian species in a basal nutrient medium supplemented with normal serum at below about 0.5% and glucose at below about 1 mM, allowing the IPSCs to grow for at least about 3 weeks, and initiating cellular differentiation into mature islet cells by re-feeding the IPSCs in culture with a nutrient medium supplemented with normal serum at about 0.5–10% and glucose at about 2.5 mM–10 mM. The pancreatic cells may be from any mammal, including humans and mice, and the serum is from the same species. The medium preferably contains all of the amino acids essential to growth of cells from the species being cultured and in such quantity as to ensure that the culture does not become depleted. Upon re-feeding, the re-feed medium preferably contains glucose and serum in sufficient quantities to stimulate differentiation. Furthermore, according to this method, once differentiation has begun, the cells are preferably re-fed frequently (about once per week). This method produces islet cells and islet-like tissue structures.

This method also provides a source of endocrine hormones, including but not limited to insulin, glucagon and somatostatin, which can be recovered from the IPSC culture medium or which can be directly released into a mammal by implantation of the islet-like structures into the tissue of a mammal to produce a pancreas-like structure. Such implantation provides a method for treating pancreatic disease in a mammal by implanting an islet-like structure to produce a pancreas-like organ in the mammal. In one embodiment, the islet cells or islet-like structure of this invention is genetically modified so as to not produce IDD autoantigens or HLA markers such that it does not express insulin dependent diabetes associated autoantigens, other than insulin, or which has been modified so that it does not express human leukocyte antigens, as said stem cell differentiates into said pancreas-like organ. Furthermore, the pancreatic stem cell may be encapsulated in an insulin, glucagon, somatostatin and other pancreas produced factor permeable capsule. Also provided is a method for analyzing the differentiation of pancreatic stem cells which comprises culturing at least one pancreatic stem cell in vitro, and inducing said at least one stem cell to begin differentiation into a pancreas-like structure. This method also permits identification of mRNA or protein markers specific to a plurality of different stages in the differentiation process. The protein markers may be expressed on the cell-surface, be secreted, or they may be intracellular. In another aspect of this invention a ligand binding molecule and a method for making a ligand-binding molecule which selectively binds to pancreatic stem cells or to more differentiated pancreatic cells is provided. The method comprises contacting a naive B-lymphocyte or T-lymphocyte with an identified protein marker, and culturing and expanding the B-lymphocyte or T-lymphocyte to obtain a population of cells which produce the ligand-binding molecule. These ligand-binding molecules thus provide a method of isolating a pancreatic stem cell or partially differentiated pancreatic cells at any stage between that of a pancreatic stem cell and a fully differentiated pancreatic cell. This method comprises selecting the cell from a population of cells comprising the cell, with a specific ligand-binding molecule which binds to a protein marker expressed by the cell at a given stage of differentiation. Alternatively, the method comprises selecting and removing other cells from a population of cells comprising the cell with a specific ligand binding molecule which binds to a protein marker absent on the surface of the cell. In yet another aspect, this invention provides a method for treating a mammal suffering from, or at risk of IDD, which comprises:

a. removing pancreatic tissue from the mammal;

b. culturing pluripotent pancreatic cells present in the pancreatic tissue in vitro to generate islet-like structures; and c. implanting said islet-like structures into said mammal.

In a further aspect of this invention, there is provided an IPSC modified so as not to express insulin dependent diabetes autoantigens in either the undifferentiated or in the differentiated state of the IPSC. Preferably, the autoantigen which is not expressed as a result of the modification is selected from GAD, 64 kD islet cell antigen, and HLA markers.

As part of the method of this invention, a method for in vitro neogenesis of islets from pluripotent stem or progenitor cells is provided which comprises:

a. establishing a stromal, or "nurse", cell monolayer of ductal pancreatic epithelial cells which permits the generation of IPSCs;

b. inducing stem/progenitor cell proliferation with culture conditions which promote cyclical regeneration of IPSCs and also prevent premature differentiation of the IPSC; and c. expanding and differentiating the IPSCs to produce an islet-like structure comprising α, β, and δ cells. Preferably, the culture-generated islet-like structure is characterized by large, differentiated cells which stain with insulin-specific stain in the center of the islet-like structure; small differentiated cells which stain with glucagon-specific stain at the periphery; and proliferating and undifferentiated cells which do not stain with any of the endocrine hormone-specific stains in the inner cortex. The structure is further characterized in that, upon breaking the structure into single cell suspensions by mechanical or other means in the presence of a proteolytic enzyme and subsequent staining of individual cells, individual cell populations which stain either with glucagon-specific stain (α cells), insulin-specific stain (β cells) or somatostatin-specific stain(δ cells) are observed. The method of in vitro neogenesis of islets according to this invention preferably comprises:

a. dispersing and leaving undisturbed pancreatic cells in a minimal culture medium comprising little or no glucose, serum at a concentration below about 0.5%, essential amino acids for the cells of the species from which the pancreatic cells were obtained, and a lipid source, until about 99% of the cells in said culture have died (phase I);

b. re-feeding the culture of step (a) with the minimal medium supplemented with about 1–10 mM glucose and about 0.5%–10% serum (but less than a toxic amount) and re-feeding about once a week until rapid proliferation occurs;

c. re-feeding the culture of step (b) with the minimal medium supplemented with 0.5%–10% serum and about 10–25 mM glucose and, optionally, added growth or cellular factors (phase III);

d. allowing islet-like structures to bud into the medium;

e. recovering the islet-like structure.

This process may be repeated several times by serially transferring epithelial cells plus early-stage, proliferating islet-like structures in culture in vitro.

As used herein, the term "growth" refers to the maintenance of the cells in a living state, and may include, but is not limited to, the propagation and/or differentiation of the cells. The term "propagation" refers to an increase in the number of cells present in a culture as a result of cell division.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing of Functional Islets of Langerhans

Figure 1A:
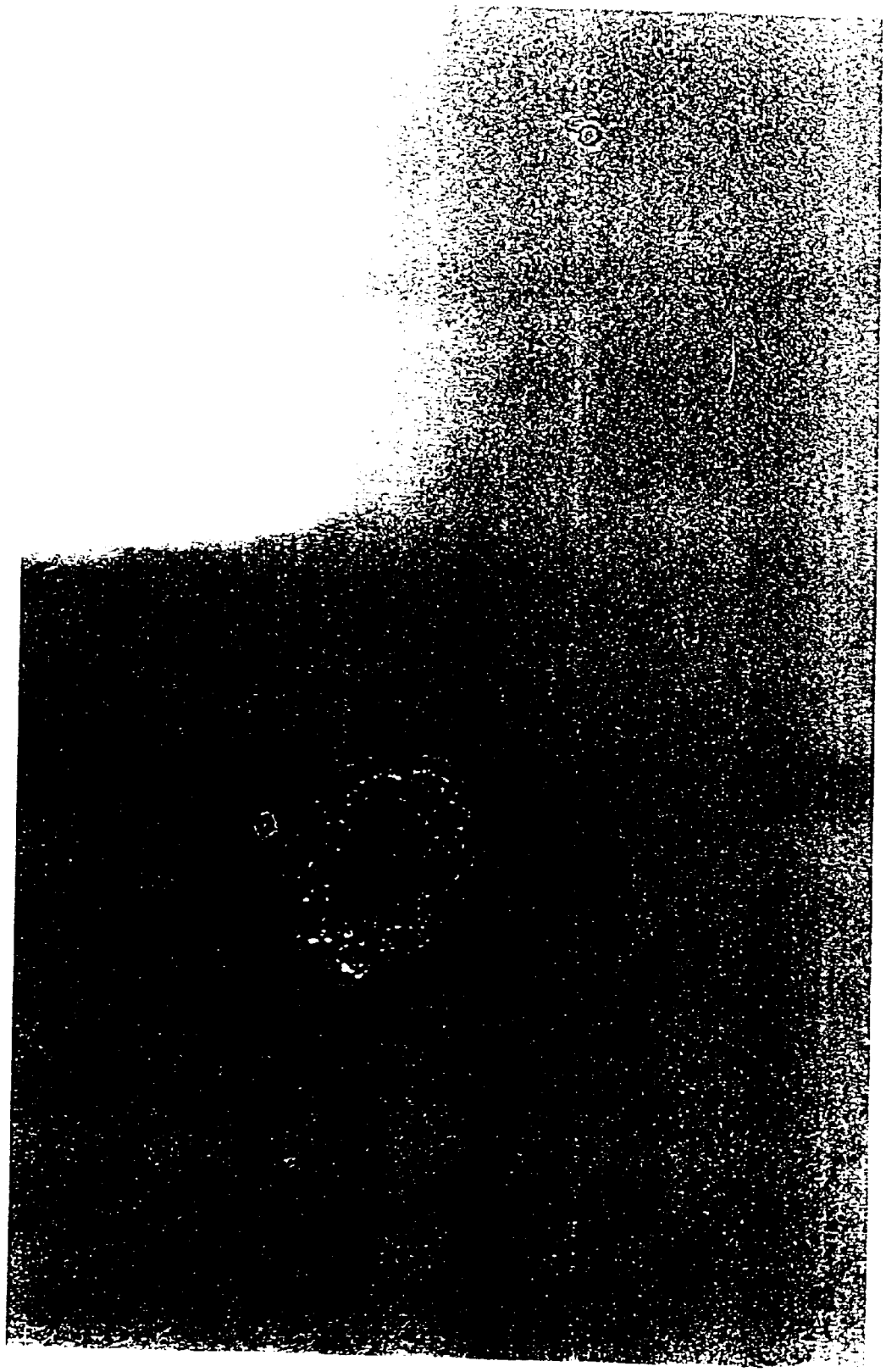
FIGS. 1A through 1D show cells grown according to the procedures of the subject invention.

Single cell suspensions of islet cells were prepared from whole islets isolated from the pancreas of 19–20 week old prediabetic male NOD/UF mice, as detailed elsewhere (Shieh et al., 1993). Typically, about 25% of the male mice in a NOD colony will have overt IDD at this age and all will have severe insulitis. The islet cells were re-suspended in glucose depleted or glucose-free Click's EHAA medium (Peck and Bach, 1973, supra; Peck and Click, 1973) supplemented with normal mouse serum (NMS) to 0.25%, plated in a 25 cm$^2$ tissue culture flask, and incubated at 37° C. in a 5% $CO_2$ atmosphere. At this stage, two outcomes are possible: first, the islet-infiltrating cells may dominate, thus permitting the establishment of immune cell lines, or second, ductal epithelial cells (often referred to as stromal cells in these cultures) may dominate, thus allowing the growth of a "nurse cell" monolayer. Growth of stromal-like cell monolayers appeared to result when islet-infiltrating cells were plated simultaneously but in limited numbers. Enrichment of the islet cells with decreased numbers of infiltrating cells can be achieved by gradient Separation (Jarpe et al., 1991, supra). The vast majority (>99%) of the origiral cells die during this incubation period, leaving a small number of epithelial-like cells attached to the culture dish (FIGS. 1A and 3A, Stage I). Stromal cell cultures, when left undisturbed for 4–5 weeks (i.e., no re-feeding) proliferated to cover the entire bottom surface of the culture vessel (FIGS. 3C and 3D).

Figure 1B:
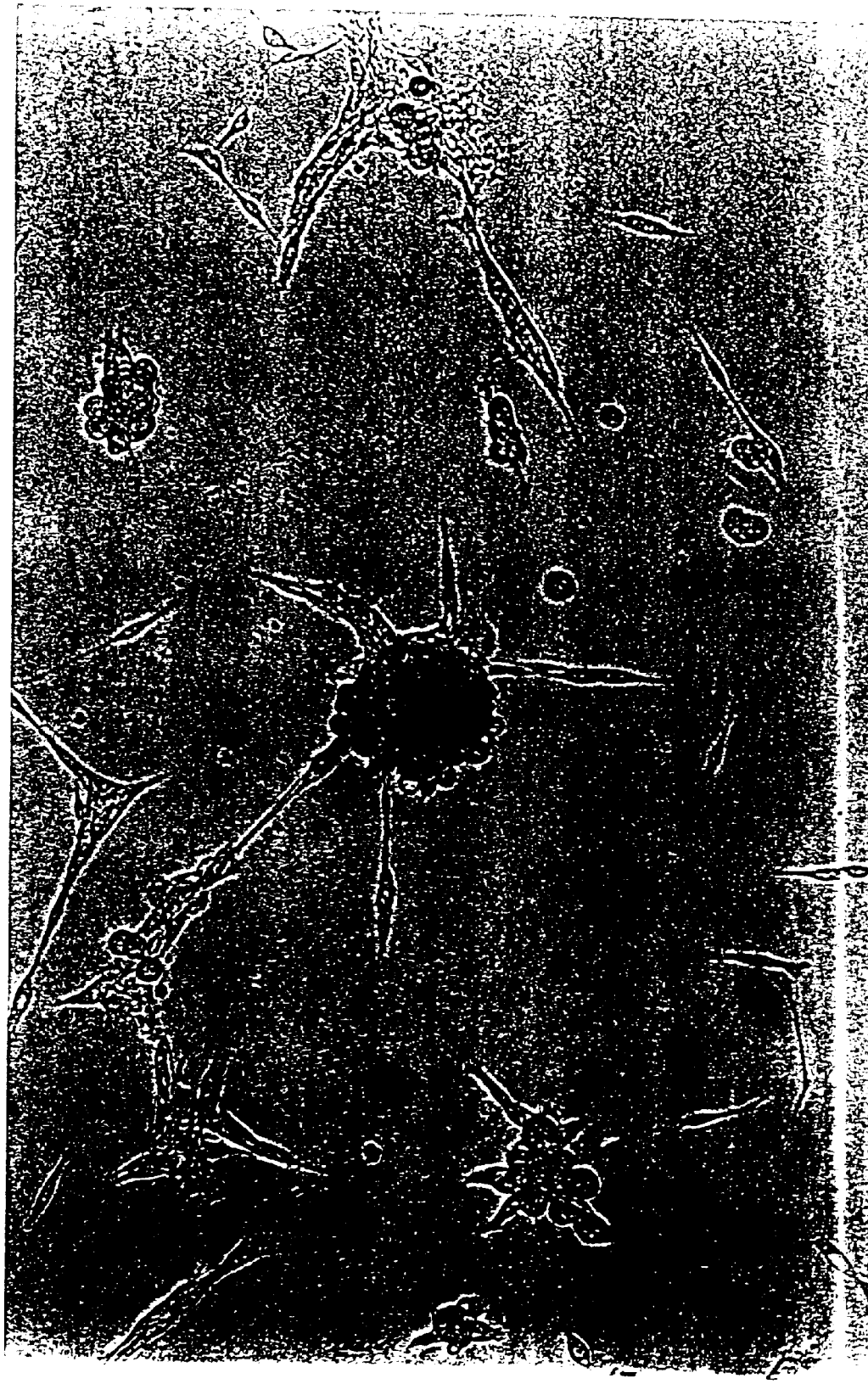
Figure 1C:
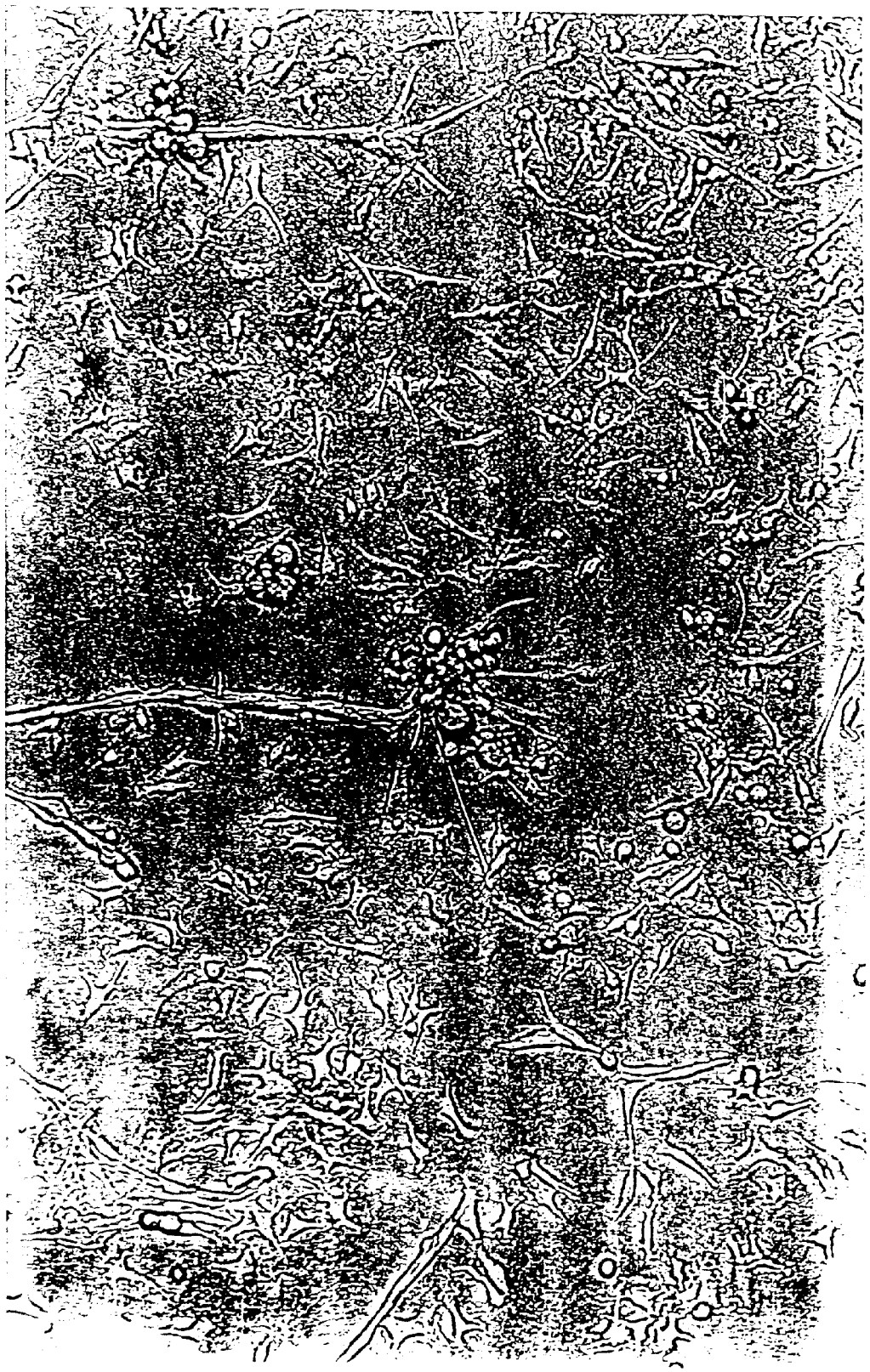
Figure 1D:
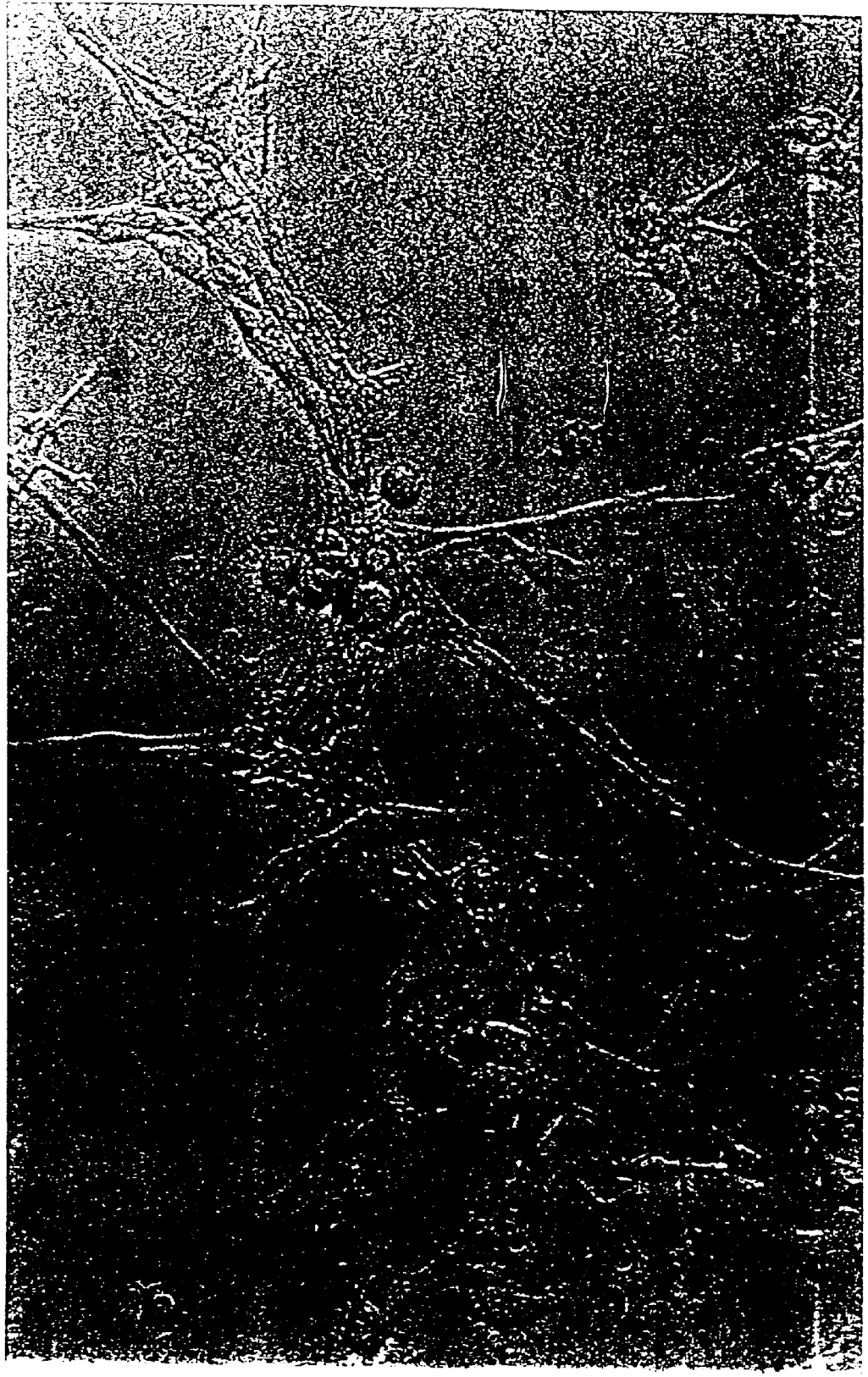

Differentiation and endocrine hormone expression of the cultures was initiated by re-feeding the cultures with Click's EHAA medium supplemented with NMS and a sugar solution comprising glucose or sucrose or other sugar equivalents. Typically, the sugar is glucose. The concentration of glucose can be between about 0.25 mM to about 10 mM, but typically is about 2.5 mM. Normal NCD or NMS serum at about 0.5% is also preferably included. Techniques for re-feeding cell cultures in vitro are well known in the art and typically involve removing from about 50% to about 90% of the old nutrient medium and adding fresh medium to the culture flask. Rapid re-feeding induced the formation of increasing numbers of centers of islet growth (referred to herein as foci) exhibiting cell differentiation. The rate of re-feeding can be, for example, at about one week intervals. Preferably, the rate of re-feeding is at about 5 to 6 day intervals. Small rounded cells appeared on top of the epithelial monolayers, almost as if by budding (FIGS. 1B and 3D, Stage II). At peak production, as many as 50–100 foci occurred simultaneously in a single 25 $cm^2$ (4 $in^2$) tissue culture flask. Each individual rounded cell underwent rapid proliferation, with the daughter cells forming cell clusters (FIG. 1C). Rapid refeeding induced increasing numbers of cell clusters as well as increased numbers of cells within each cluster. Induction of islet-like structures (Stage III) was enhanced through re-feeding of cultures with EHAA medium supplemented with normal mouse serum (0.5%) and high levels of glucose (10 mM–25 mM and preferably about 16.7 mM glucose—See FIG. 1D and 3E–3F). As the cell proliferation and differentiation proceeded, the organization of the islet took place and the islet even appeared to surround itself with a capsular material. Mature islets (Stage IV) appeared as smooth spheroids composed of tightly clustered cells (FIG. 3F–3H). This differentiation appears to be enhanced when serum from NOD mice is used rather than serum from other strains of mice, and higher levels of insulin-like growth factor (IGF), epidermal growth factor (EGF) and/or hepatocyte growth factor (HGF) in the NOD mouse serum are believed to be responsible for this effect. The islets generally grew to a constant size (about 100–150μ, FIG. 2, although fusion of two clusters resulted in islets about twice the general size), then detached off of the stromal layers to float in the medium. These free-floating islets tended to break down within 48–72 hours, similar to what is observed when pancreatic islets are isolated from in vivo sources and then cultured under similar conditions. Serial rounds of this process may then be conducted (see FIG. 6A–6D and Example 5 below).

Figure 2:
FIG. 2 shows an islet-like structure grown according to the subject invention.

The islet-like structures, collected after natural detachment or removal from the stromal layers using a Pasteur pipette, were gently washed in medium, then broken into single cell suspensions by reflux pipetting. Single cell suspensions were prepared by cytocentrifugation, then stained for general morphology and insulin production. The foci contained cells producing the endocrine hormones glucagon (α cells), insulin (β cells) and/or somatostatin (δ cells). Furthermore, the major population of cells stained positive with anti-insulin antibody, indicating the major cell type contained in the cultured islet is an insulin-producing β cell. FIGS. 1A through 1D show the various cell types which develop during the culture process. FIG. 2 shows a well-developed islet obtained after the in vitro culture of cells according to the method of the subject invention.

EXAMPLE 2

Culturing of Human Islet Cells

For culturing human islet cells, a procedure similar to that described in Example 1 was utilized. The procedure of the subject invention is particularly advantageous because it is not necessary to utilize fetal cells to initiate the cell culture. In a preferred embodiment, the human cells can be suspended in Click's EHAA medium (or the equivalent thereof) supplemented with normal human serum. Preferably, the concentration of normal human serum used in the medium is about 0.25%–1% in phases I and II, respectively, and 5% during subsequent phases. The cultures should be left undisturbed with no re-feeding, preferably for several weeks (phase I). After about 4–5 weeks in culture, cell differentiation can be initiated by re-feeding the cultures with Click's EHAA medium supplemented with normal human serum and glucose as described in Example 1. Islet-like structures can subsequently be collected and single cell suspensions prepared for further propagation as described in Example 1.

EXAMPLE 3

Implantation of in vitro Grown Islet Cells

To test the efficacy of these in vitro generated islet-like structures to reverse the complications of IDD, approximately 150–200 foci plus some stromal cells grown in vitro according to the method of the subject invention from pancreatic tissue of NOD mice were dislodged from the tissue culture flask by reflux pipetting. The cells were then implanted beneath the kidney capsule of syngeneic diabetic NOD mice maintained by daily insulin injections. Implantation was accomplished by puncturing the kidney capsule with a hypodermic needle, threading a thn capillary tube through the puncture site into the kidney, and injecting the islet foci directly into the cortex region. The capillary tube was carefully withdrawn and the puncture site cauterized. The surgical incision of each implanted mouse was clamped until the skin showed signs of healing. The implanted mice were maintained on insulin injections for 4 days at the full daily dosage, and then for 2 days at the half daily dosage, after which the mice were completely weaned from further insulin treatment. Control animals consisted of diabetic NOD mice that did not receive an implant.

Figure 7:
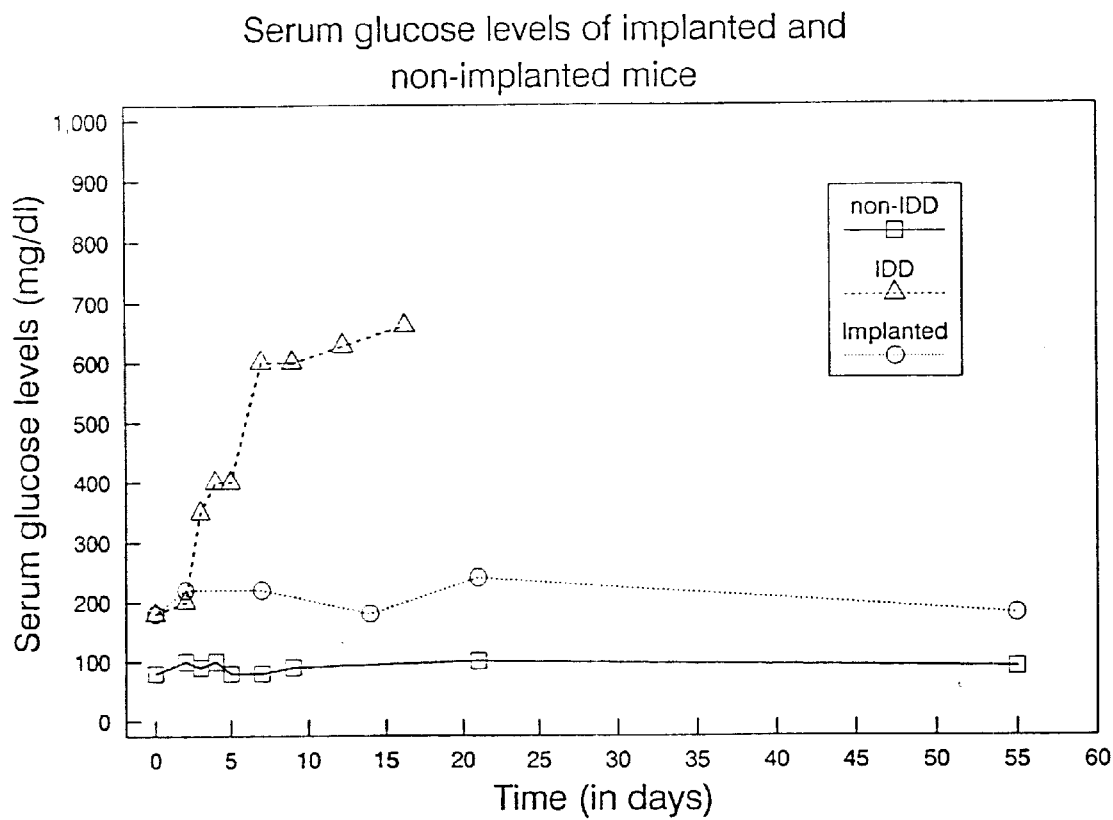
FIG. 7 shows data from control and implant NOD mice after cessation of insulin therapy.

Within 8–14 days after weaning from insulin, control NOD mice showed a rapid onset of overt disease, including lethargy, dyspnea, weight loss, increased blood glucose levels (400–800 mg/dl), wasting syndrome, failure of wound healing and death within 18–28 days (FIG. 7). Implanted NOD mice maintained a blood glucose level of about 180–220 mg/dl (which is slightly above the normal range for mice), showed increased activity, rapid healing of surgical and blood-draw sites, did not develop dyspnea, and remained healthy until killed 55 days post-implant for histological studies (FIG. 7). Similar observations have been seen with intra-splenic implants. These data are consistent with the concept that the implanted in vitro-generated islets provide the necessary insulin to maintain stable blood glucose levels over the time course of the experiment.

EXAMPLE 4

In vivo Production of Ecto-Pancreas

Figure 8:
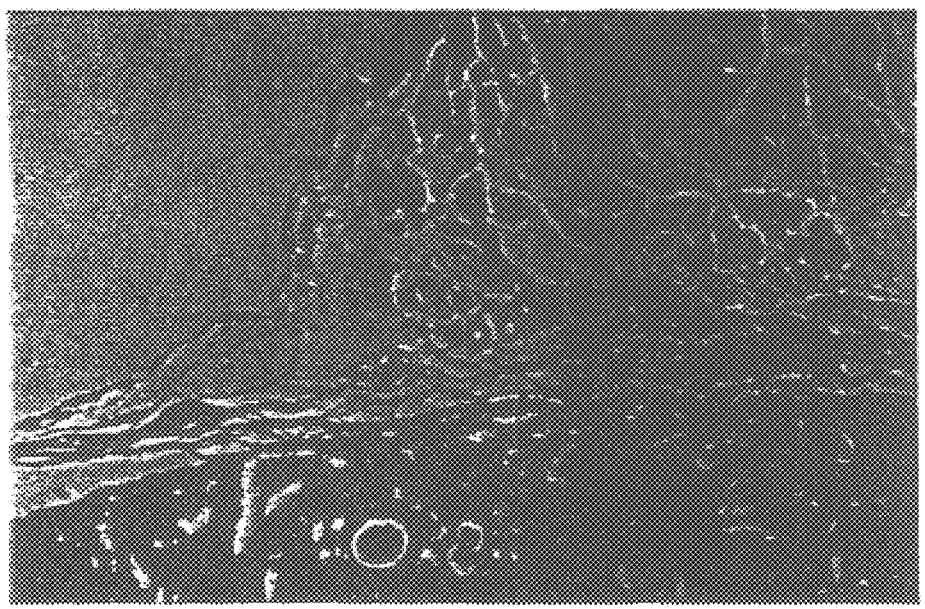
FIG. 8 shows an ecto pancreas.
Figure 8:
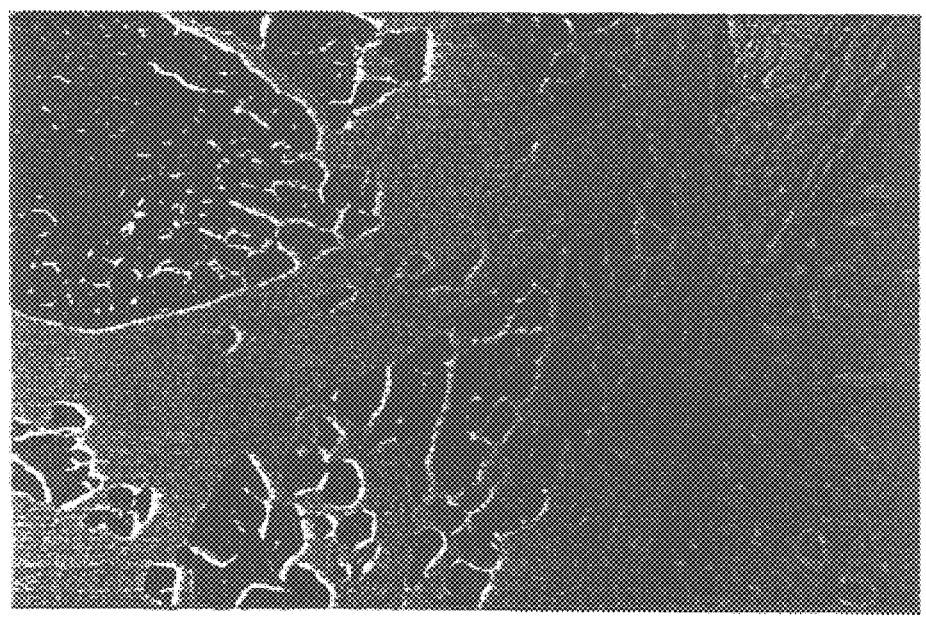

Histological examinations of the implant sites in mice that were implanted with the islet cells as described in Example 3 revealed an additional characteristic of the in vitro generated islet-forming stem cells. Implanted cells which "leaked" from the implant site of the kidney underwent additional proliferation and differentiation and formed a highly structured ecto-pancreas. At first, the ecto-pancreatic tissue consisted entirely of proliferating exocrine cells which organized into an exocrine pancreas complete with innervating blood vessels. This exocrine pancreas progressed to form islet-like endocrine structures (see FIG. 8). Thus, the in vitro cell cultures produced according to the methods of the subject invention contain pluripotent pancreatic stem cells capable of regenerating a completely new pancreas. The growth of a pancreas containing both exocrine and endocrine tissue provides new methods for treatment of pancreatic diseases, including pancreatitis and pancreatic cancer.

EXAMPLE 5

Long Term Propapation of IPSCs

Figure 6:
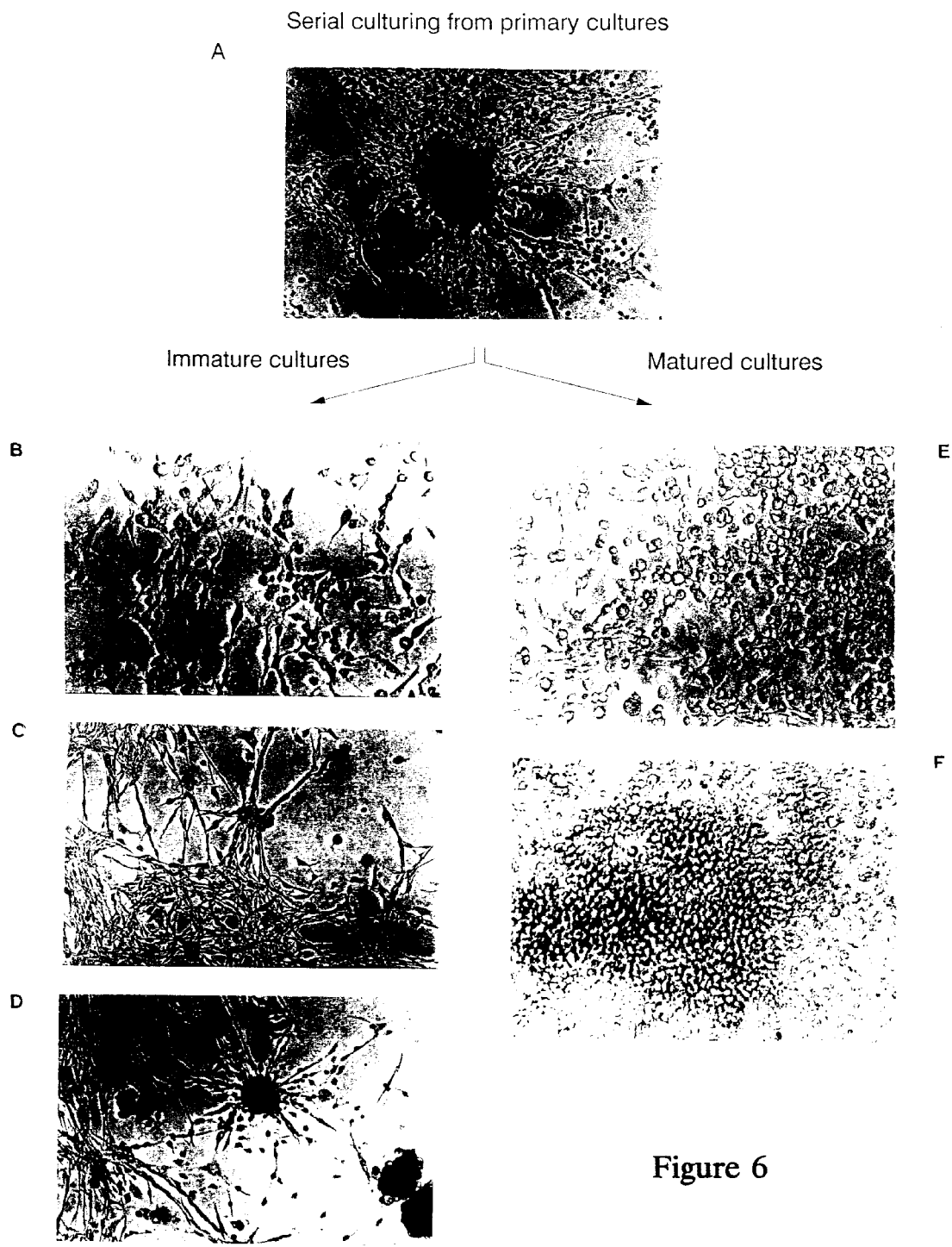
FIG. 6A through 6F shows a series of micrographs in which an islet-like structure, such as that shown in FIG. 3H, is harvested from a primary culture.

Long term propagation (>1 year) of the IPSCs was achieved through serial transfers of small numbers of the epithelial cells plus a few early-stage, proliferating islet-like structures to new culture flasks. Cells from a single 25 cm$^2$ tissue culture flask have been expanded successfully to 5–10 150 cm$^2$ tissue culture flasks. Interestingly, serial transfer uniformly resulted in the islet structures "melting" away, similar to the detached islet-like structures, while new stromal monolayers formed (FIG. 6A–6B). However, serially transferred cultures produced new islets far sooner than primary cultures and in higher number (as many as 200–250 structures per square inch of culture-FIGS. 6C–6D). However, eventually, after many rounds of serial growth and production of islet-like structures, a point is generally reached where after the islet-like structure "melts", only differentiated cells proliferate (see FIGS. 6E–6F). The same thing can occur, in the absence of observable islet-like structure formation, if primary pancreatic tissue is grown in primary culture under conditions which do not kill most of the differentiated cells.

EXAMPLE 6

Analysis of Islet-Like Structures

Photomicrographics of serial sections of immature, culture-generated islet-like structures and sections thereof (shown in FIGS. 4 and 5, respectively) again demonstrate the uniformity of growth. Large, somewhat differentiated cells which stain weakly with insulin are observed in the islet center. Small differentiated cells which stained with glucagon were apparent at the periphery, while a significant number of immature, proliferating, and undifferentiated cells which did not stain with any of the endocrine hormone antibodies were present in the inner cortex. To determine more precisely the cell phenotypes present within the in vitro grown islets, the islet-like structures were collected following detachment from the epithelial monolayers, gently washed in medium, then broken into single cell suspensions by mechanical means, such as reflux pipetting in the presence of a proteolytic enzyme such as 0.25% trypsin. Slides of single cell suspensions were prepared by cytocentrifugation and stained for general morphology or cellular content. Several morphologically distinct mature and immature cell types are observed following H/E staining. Furthermore, individual cell populations stained with either anti-glucagon (α cells), anti-insulin (β cells) or anti-somatostatin (δ cells) antibodies, indicating the pluripotent nature of the stem/progenitor cells giving rise to the islet-like structures. These observations emphasize two points: first, the weak staining for endocrine hormones suggests the cells of in vitro-generated islets remain relatively immature, and therefore capable of further differentiation upon in vivo implantation, and second, the fact that >100% of the cells could be accounted for by endocrine hormone staining indicates that some cells must express both glucagon and insulin simultaneously, as reported recently by Teitelman et al. (Teitelman et al., 1993, supra).

EXAMPLE 7

Limiting Dilution of Pancreatic Cells—Cloning of Single Pancreatic Stem Cells

According to the methods described above, pancreatic tissue is dispersed in a culture medium. To isolate single stem cells for clonal production of differentiated pancreatic cells, the dispersed pancreatic cells are subjected to limit dilution according to methods well known in the art. Thus, for example, serial ten-fold dilutions are conducted after an initial evaluation of the number of cells/mL in the dispersed sample, such that the final dilution yields, at the most, an average of 0.3 cells per microtiter well or other container suitable for this type of dilution experiment. Thereafter, the cells are allowed to remain undisturbed until foci begin to develop. These foci are stem cells which have each arisen from a single pluripotent stem cell or IPSC and which can each be cultured to yield an islet-like structure for implantation to form a pancreas-like structure.

EXAMPLE 8

Identification of Markers Associated With Different Stages of Pancreatic Stem Cell Differentiation, and Production of Ligand Binding Molecules Specific to Each Stage of Differentiation Foci of isolated stem cells produced according to Example 7 or by an analogous method are analyzed both prior to and after induction of differentiation according to Example 1 or by a similar method. The cells at each stage, from stem cell to fully committed differentiated pancreatic cells, are analyzed as follows:

A. Nucleic Acid: At each stage of differentiation, including the undifferentiated progenitor cells and the fully differentiated pancreatic cells, mRNA is isolated. This RNA is used to make cDNA according to standard methods known in the art (Maniatis et al., 1982) including but not limited to PCR dependent amplification methods using universal primers, such as poly A. Each amplification represents a library of message expressed at each stage of pancreatic stem cell development. Accordingly, message not present in stem cells but present in fully differentiated pancreatic cells is identified by hybridizing the cDNA from each stage and isolating message that remains unhybridized. Likewise, methods such as differentiated display PCR, arbitrarily primed PCR or RDA-PCR (see above) may be used. In this manner, message unique to each stage is identified by subtraction of message present at other stages of differentiation. Also, by this method, gene products produced at each stage of the differentiation process are identified by expressing the product encoded by the subtracted message. Antibodies, including monoclonal antibodies, are then produced by using these gene products as antigens according to methods well known in the art (see Goding, J. W., 1986). These antibodies are subsequently used to isolate cells from any given stage of differentiation based on affinity for markers expressed on the cell surface of the pancreatic cell. In addition, identification of specific markers which are expressed on the surface of the differentiated pancreatic cells allows production of knock-out lines of pancreatic cells by site-directed mutagenesis using the identified sequences to direct mutations in stem cells according to methods such as those disclosed in U.S. Pat. Nos. 5,286,632, supra; 5,320,962; 5,342,761; and in WO 90/11354; WO 92/03917; WO 93/04169; and WO 95/17911. Selection of mutant cells which do not produce the knocked-out gene product is accomplished using the antibodies to the specific gene product selected against to provide clones of cells in which that product is absent.

B. Protein Markers: At each stage of differentiation, including the undifferentiated progenitor cells and the fully differentiated pancreatic cells, antibodies are generated to whole cells and subcellular fractions, according to standard methods known in the art. As specific examples of this process:

a) Production of rat anti-mouse IPSC mAbs: To enhance selection of B lymphocytes activated against IPSC-specific antigens, rats are immunized with normal mouse tissue followed by treatment with cyclophosph.amide on day 7 post-immunization. Cyclophosphamide selectively kills the reactive B cells, leaving the rats unresponsive to normal mouse antigens. On day 14 post-immunization, the rats are re-challenged with cells collected from various stages of mouse IPSC cultures. Three to four weeks after this secondary challenge, the rats are re-immnunized with IPSC culture cells for three days, then fused with the SPO/2 mycloma partner. Positively reacting antibodies are selected and cloned.

b) Production of mouse anti-human IPSC mAbs: Mouse anti-human IPSC mAbs are prepared using the same procedure as described above for the production of rat anti-mouse mAbs, except that mice are immunized with normal human tissue and then re-challenged after cyclophosphamide treatment with cells from various stages of human IPSC cultures.

c) Use of anti-IPSC mAbs in the Identification of Various Differentiation Stages of Islet Cell Growth: The mAbs raised against IPSC cultured cells are used to sort by FACS or any other means known in the art, such as in magnetically stabilized fluidized beds (see below), the various cell populations defined by these reagents. Sorted cell populations are examined for their stages of differentiation (e.g., co-expression of insulin, glucagon, somatostatin, β-galactosidase, tyrosine hydroxylase, the Reg-gene to name a few) and their growth capacity (e.g., their ability to initiate IPSC cultures).

Reagents which define cell surface and differentiation marks of cells involved in the neogenesis of islets are useful for the scientific community in this area of research. In addition, such reagents greatly facilitate the isolation (or enrichment) of IPSCs per se. Isolation of IPSCs permits testing of the efficacy of re-implanting IPSCs instead of whole islets into IDD patients, or even implantation directly into the pancreas, circumventing the need for extra-pancreatic implants.

In addition, these antibodies are used to isolate cells from any given stage of differentiation based on affinity for markers expressed on the cell surface of the pancreatic cell. Identification of specific markers which are expressed on the surface of the differentiated pancreatic cells allows production of knock-out lines of pancreatic cells. Cells which do not produce the undesirable gene product are selected by using the antibodies to select for clones of cells in which that product is absent. In an analogous fashion, markers significant tD T-cell recognition and destruction of differentiated pancreatic cells are identified by activating naive T-cells with whole pancreatic cells or subcellular fractions thereof, across the differentiation process. Identification of markers significant to T-cell activation allows subsequent modification of the stem cells to eliminate these markers and thereby produce cells which, in the differentiated state, are resistant to autoimniune destruction.

EXAMPLE 9

Isolation of Pancreatic Cells at Different Stages of Differentiation

Using the markers and ligand-binding molecules identified according to Example 8, pancreatic stem cells or partially or completely differentiated pancreatic cells can be isolated according to methods well known in the art. Accordingly, the methods for hematopoietic stem cell isolation disclosed in U.S. Pat. Nos. 5,061,620; 5,437,994; 5,399,493; in which populations of pure stem cells are isolated using antibodies to stem cell markers, are hereby incorporated by reference as if fully set forth herein. Likewise, the methods for mammalian cell separation from mixtures of cells using magnetically stabilized fluidized beds (MSFB), disclosed in U.S. Pat. No. 5,409,813, are hereby incorporated by reference as if fully set forth herein. Antibodies to markers identified at each stage of pancreatic stem cell differentiation are attached to magnetizable beads, and cells are passed through the magnetically stabilized fluidized bed. Cells which adhere to the antibody bound magnetizable beads, or cells which flow through the bed, are isolated.

Any of a number of other methods known in the art for isolation of specific cells may be used for this purpose. These methods include, but are not limited to, complement destruction of unwanted cells; cellular panning; immunoaffinity chromatography; elutriation; and soft agar isolation techniclues (see Freshrey, R. I., 1988).

EXAMPLE 10

Analysis of Factors Which Trigger Pancreatic Stem Cell Differentiation and Factors Produced at Different Stages of Stem Cell Differentiation Cells isolated according to the methods of Example 9 or like methods are cultured according to the method of Example 1 or like culturing method. Factors significant in inducing differentiation are assayed by adding different factors to the growth medium and observing the differentiation inducing effect on the cells. Thus, conditioned culture media from various cells can be tested, and factors which cause pancreatic stem cell differentiation are isolated using induction of differentiation as a purification assay. Other factors such as glucose, other chemicals, hormones and serum fractions are similarly tested to isolate the significant differentiation inducing factors.

Factors produced at different stages of differentiation are isolated and analyzed from the conditioned culture medium of cells at each stage of the differentiation process. These factors are likewise tested for their autocrine effect on stem cells and further differentiation of partially differentiated stem cells.

EXAMPLE 11

Genetic Modification of Pancreatic Stem Cells to Produce Autoantibody, CTL Resistant, and HLA Modified Differentiated Pancreatic Cells Pancreatic stem cells cultured according to Example 1 or 2 or isolated according to Example 8 are subjected to genetic modification according to any method known in the art to produce autoantibody and CTL resistant stem and differentiated pancreatic cells, according to methods such as those disclosed in U.S. Pat. Nos. 5,286,632, supra; 5,320,962, supra; 5,342,761, supra; and in WO 90/11354, supra; WO 92/03917, supra; WO 93/04169, supra; and WO 95/17911, supra. Alternatively, selection of resistant stem cells is accomplished by culturing these cells in the presence of autoantibody or IDD associated CTLs or CTLs activated with IDD specific autoantigens. As a result of these techniques, cells having increased resistance to destruction by antibody or T-lymphocyte dependent mechanisms are generated. Such cells are implanted into an appropriate host in an appropriate tissue as disclosed above in Examples 3 and 4 to provide a pancreas-like structure which has increased resistance to destruction by autoimmune processes.

Likewise, the human leukocyte antigen profile of the pancreatic stem cell and differentiated cell is modified, optionally by an iterative process, in which the stem cell is exposed to normal, allogeneic lymphocytes, and surviving cells selected. Alternatively, a site directed mutagenesis approach is used to eliminate the HLA markers from the surface of the stem or differentiated cells, and new stem cells thereby generated or isolated from pancreas-like structures are used to implant into a recipient mammal in need of such implantation.

In a specific example, the adeno-associated virus (AAV) vector system carrying the neomycin-resistance gene, neo is used. AAV can be used to transfect eukaryotic cells (Laface, 1988). In addition, the pBABE-bleo shuttle vector system carrying the phleomycin-resistance gene is used (Morgenstein, 1990). Ihis shuttle vector can be used to transform human cells with bacteria-derived genes.

a) Transfection of IPSCs: Cultured IPSCs are transfected with either the retroviral segment of the pBABE-2-bleo vector by electroporation or the AAV-neo vector by direct infection. Adherent cells from established IPSC cultures are removed gently from the tissue culture flasks using C-PEG buffer (phosphate buffered saline supplemented with EDTA and high glucose). These cells are suspended in DMEM and 10% fetal rat serum containing the retroviral stock, and in the case of pBABE-bleo, subjected to electroporation. (Since electroporation can be a fairly harsh procedure compared to direct viral infection, the cells subject to electroporation are examined for viability. Viability of the IPSC culture cells is determined by their ability to exclude vital dye and analysis of injury-associated cell products such as glycosaminoglycans and hydroperoxides.) secondary cultures of the transfected cells are established. Re-cultured cells are selected for resistance to phleomycin or neomycin, respectively.

b) Identification of Pro-viral DNA in Transformed Cells: Neomycin or phleomycin resistant cultured cells are tested for the presence of the appropriate transfecting viral DNA. Cells are removed from the culture flasks using C-PEG buffer and digested in lysis buffer containing proteinase K. DNA is phenol/chloroform extracted, then precipitated in ethanol/sodium acetate. Proviral DNA is identified using nested PCR. For the first reaction, PCR primers are used which amplify the entire open reading frame of the appropriate resistance gene. For the second PCR reaction, the PCR product is used as template. Selected internal 5' and 3' primers are used which amplify an internal sequence of known base pair size. The final PCR product is detected by ethidium bromide staining of agarose gels following electrophoresis and/or probing of Southern blots.

c) Stability of Transformation: The long-term stability of the transformations is determined by maintaining long-term growing cultures of the transfected cells and periodically testing them for the presence of pro-viral DNA, as described above.

These studies provide information on the efficacy and reproducibility of transfection procedures using IPSCs as target cells. Furthermore, they establish a sound foundation for use of transformed IPSCs in treating IDD patients.

EXAMPLE 12

Encapsulation of in vitro generated islets and Implantation Into a Mammal

Methods for encapsulation of cells are well known in the art (see, for example, Altman, et al., 1984, *Trans. Am. Soc.* *Art. Organs* 30:382–386, herein incorporated by reference, in which human insulinomas were enclosed in selectively permeable macrocapsules). Accordingly, isolated in vitro generated isl(ts, optionally genetically modified according to Example 11, or pancreas-like structures produced according to examples 3 and 4, are encapsulated in an insulin, glucagon and somatostatin permeable encapsulant. Preferably such encapsulant is hypoallergenic, is easily and stably situated in a target tissue, and provides added protection to the implanted structure such that differentiation into a functional entity is assured without destruction of the differentiated cells.

It should be understood that the examples and emboliments described herein are for illustrative purposes only and that various modifications or changes in light thereof will be suggested to persons skilled in the art and are to be included within the spirit and preview of this application and the scope of the appended claims.

References

Eisenbarth, G. S., (1986) *N. Engl. J. Med.* 314:1360.
Cahil, G. F., and H. O. McDevitt (1981) *N. Engl. J. Med.* 304:1454.
Todd JA, J. A., et al. (1989) *Nature* 338:587.
Prochazka, M., D. V. Serreze, S. M. Worthen, and E. H. Leiter (1989) *Diabetes* 38:1446.
Baekkeskov, S., et al., (1982) *Nature* 298:167.
Baekkeskov, S., et al. (1990) *Nature* 347:151.
Reddy, S., N. J. Bibby, and R. B. Elliot (1988) *Diabetologia* 31:322.
Pontesili, O., P. Carotenuto, L. S. Gazda, P. F. Pratt, and S. J. Prowse (1987) *Clin. Exp. Immunol.* 70:84.
Wang, Y., L. Hao, R. G. Gill, and K. J. Lafferty (1987) *Diabetes* 36:535.
Karjalainen et al. (1992) *N. Engl. J. Med.* 327:302.
Serreze, D. V., E. H. Leiter, E. L. Kuff, P. Jardieu, and K. Ishizaka (1988) *Diabetes* 37:351
Signore, A, P. Pozzilli, E. A. M. Gale, D. Andreani, and P. C. L. Beverly (1989) *Biabetologia* 32:282.
Jarpe, A. J., M. Hickman, J. T. Anderson, W. E. Winter, and A. B. Peck (1991) *Regional Immunol.* 3:305
Bendelac, A., C. Carnaud, C. Boitard, and J. F. Bach (1987) *J. Exp. Med* 166:823.
Gazdar et al. (1980) *P.N.A.S.* 77(6):3519–3525.
Brothers, A. J., PCT Application WO 93/00441, published Jan. 7, 1993.
Korsgren et al. (1993) *J. Med. Sci.* 98(1):39–52.
Nielson, J. H., PCT Application WO 86/01530, published Mar. 13, 1986.
McEvoy et al. (1982) *Endocrinol.* 111(5):1568–1575.
Zayas et al., EPO 0 363 125, published Apr. 11, 1990.
Coon et al., PCT Application WO 94/23572, published Oct. 27, 1994.
Miller, B. J., M. C. Appel, J. J. O'Neil, and L. S. Wicker (1988) *J. Immunol.* 140:52.
Hanafusa T. et al. (1988) *Diabetes* 37:204.
Bendelac A. et al. (1988) *J. Immunol.* 141:2625.
Rossini, A. A., J. P. Mordes, and E. S. Handler (1988) *Diabetes* 37:257.
Nerup, J., et al. (1989) *Diabetes Care* 11:16.
Kanazawa, Y., et al. (1984) *Diabetologia* 27:113.
Anderson, J. T., J. G. Cornelius, A. J. Jarpe, W. E. Winter and A. B. Peck (1993) *Autoimmunity* 15:113.
Shieh, D. C., J. G. Cornelius, W. E. Winter, and A. B. Peck (1993) *Autoimmunity* 15:123.
Peck, A. B. and F. H. Bach (1973) *J. Immunol. Methods* 3:147.

Peck, A. B. and R. E. Click (1973) *European J. Immunology* 3:382.
Lacey, P. E., J. Davies (1957) *Diabetes* 6:354.
Baum, J., B. E. Simons, R. H. Unger, L. L. Madison (1962) *Diabetes* 11:371.
Dubois, M. P. (1975) *P.N.A.S. (USA)* 72:1340.
Pelletier, G., R. Leclerc, A. Arimua, A. V. Schally (1975) *J. Histochem, Cytochem.* 23:699.
Larsson, L. I., F. Sundler, R. Hakanson (1975) *Cell Tissue Res.* 156:167.
Brelje, T. C., D. W. Scharp, R. L. Sorenson (1989) *Diabetes* 38:808.
Pictet, R. L., W. J. Rutter (1972) in *Handbook of Physiology*, D. Steiner and N. Frienkel, eds., (Williams & Wilkins, Baltimore, Md.) pp. 25–66.
Hellerstrom, C. (1984) *Diabetologia* 26:393.
Weir, G. C., S. Bonner-Weir (1990) *J. Clin. Invest.* 85:983.
Teitelman, G., S. Alpert, J. M. Polak, A. Martinez, D. Hanaian (1993) *Development* 118:1031.
Beattie, G. M., et al. (1994) *J. Clin. Endo. Med.* 78:1232.
Bonner-Weir, S., L. Orci (1982) *Diabetes* 41:93.
Teitelman, G., S. Alpert, D. Hanahan (1988) *Cell* 52:97.
Menger, M. D., P. Vajkoczy, C. Berger, K. Messmer (1994) *J. Clin. Invest.* 93:2280.
Eisenbarth, G. S. (1986) *N. Engl. J. Med.* 314:1360.
Leiter, E. H., M. Prochazka, D. L. Coleman (1987) *Am. J. Path.* 128:380.
Bonner-Weir S., F. E. Smith (1994) *T.E.M.* 5:60.
Swenne, I. (1992) *Diabetologia* 35:193.
Hellerstrom, C., I. Swenne, A. Andersson (1988) in *The Pathology of the Endocrine Pancreas in Diabetes*, P. J. Lefebvre and D. G. Pipeleers, eds. (Springer-Verlag, Heidelberg, Germany) pp. 141–170.
Bonner-Weir, S., D. Deery, J. L. Leahy, G. C. Weir (1989) *Diabetes* 38:49.
Marynissen, G., L. Aerts, F. A. Van Assche (1983) *J. Develop. Physiol.* 5:373.
Neilsen, J. H., et al. (1992) *Adv. Exp. Med. Biol.* 321:9.
Brelje, T. C., et al. (1993) *Endocrinology* 132:879.
Weaver, C. V., R. L. Sorenson, H. C. Kuang (1985) *Diabetologia* 28:781.
Gu, D., and N. Sarvetnick (1993) *Development* 118:33.
Bonner-Weir, S., L. A. Baxter, G. T. Schuppin, F. E. Smith (1993) *Diabetes* 42:1715.
Rosenberg, L., A. I. Vinik (1992) *Adv. Exp. Med. Biol.* 321:95.
Otonkoski, T., et al. (1994) *Diabetes* 43:947.
Watanabe, T., et al., (1994) *P.N.A.S. (USA)* 91:3589.
Otonkoski, T., M. I. Mally, A. Hayek (1994) *Diabetes* 43:1164.
Payton et al. (1995) *J. Clin. Invest.* 96:1506–1511.
Jones, U.S. Pat. No. 5,286,632, issued Feb. 15, 1994.
Stiles, et al., U.S. Pat. No. 5,320,962, issued Jun. 14, 1994.
Mcleod, U.S. Pat. No. 5,342,761, issued Aug. 30, 1994.
Almond, PCI Application WO 90/11354, published Oct. 4, 1990.
Kay, et al., PCT Application WO 92/03917, published Mar. 19, 1992.
Berns, et al., PCT Application WO 93/04169, published Mar. 4, 1993.
Kucherlapti, et al., PCT Application WO 95/17911, published Jul. 6, 1995.
Durinovic, B. I., et al. (1994) *Diabetes* 43(11):1318–1325.
Elias and Cohen (1994) *Lancet* 343(8899):704–706.
Conrod et al. (1994) *Nature* 371(6495):351–385.
Santamaria et al. (1994) *Diabetes* 43(4):599–606.
Wegmann et at (1993) *J. Autoimm.* 6(5):517–527.
Liang et al. (1992) *Science* 257:967–971.
Welsh et al. (1992) *Nuc. Acid. Res.* 20:4965–4970.
Lisitsyn (1993) *Science* 259:946–951.
Altman et al. (1994) *Trans. Am. Soc. Art. Organs* 30:382–386.
Maniatis et al. (1982) Cold Spring Harbor.
Goding, J. W. (1986) "Monoclonal Antibodies: Principles and Practice," Academic Press.
Tsukamato, et al., U.S. Pat. No. 5,061,620, issued Oct. 29, 1991.
Emerson, et al, U.S. Pat. No. 5,437,994, issued Aug. 1, 1995.
Emerson, et al., U.S. Pat. No. 5,399,493, issued Mar. 21, 1995.
Freshrey, R. I. (1988) *Animal Cell Culture* 198, IRL Press.
Anderson, J. T., J. G. Cornelius, A. J. Jarpe, W. E. Winter, A. B. Peck (1993) *Autoimmunity* 15:113.
Peck, A. B., R. E. Click (1973) *Eur. J. Immunol.* 3:875.
Peck, A. B., R. E. Click (1973) *Eur. J. Immunol.* 3:385.
Teitelman, G., S. Alpert, J. M. Polak, A. Martinez, D. Hanahan (1993) *Development* 118:1031.
Otonkoski, T., M. Knip, I. Wong, O. Simell (1991) *Life Sciences* 48:2157.
Marchetti, P., et al. (1994) *Diabetes* 43:827.
Otonkoski, T., G. M. Beattie, M. I. Mally, C. Ricordi, A. Hayek (1994) *J. Clin. Endo. Met* 78:1232.
Laface, D., P. Hermonat, E. K. Wakeland, A. B. Peck (1988) "Gene transfer into hematopoietic progenitor cells mediated by an adeno-associated virus vector," *Virology* 162:483–486.
Morgenstein, J. P., H. Land (1990) "Advanced mammalian gene transfer: high titre retroviral vectors with multiple drug selection markers and a complementary helper-free packaging cell line," *Nucleic Acids Res.* 18:3587–3596.

We claim:

1. A method for the in vitro growth of islet producing stem cells, IPSCs, to produce islet cells or an islet-like structure which comprises culturing pancreatic cells from a mammalian species in a basal nutrient medium supplemented with normal serum at below about 0.5% and glucose at below about 1 mM, allowing said IPSCs to grow for at least about 3 weeks, and initiating cellular differentiation into mature islet cells by re-feeding the IPSCs in culture with a nutrient medium supplemented with normal serum at about 0.5–10% and glucose at about 2.5 mM–10 mM.

2. The method, according to claim 1, wherein the pancreatic cells are human islet cells and the serum is normal human serum.

3. The method, according to claim 1, wherein the pancreatic cells are mouse islet cells and the serum is normal mouse serum.

4. A method, according to claim 1, wherein said nutrient medium comprises a high amino acid nutrient medium.

5. The method, according to claim 1, wherein the culture medium used to re-feed said cell culture further comprises glucose.

6. The method of claim 5 wherein differentiation is enhanced by inclusion of about 10–25 mM glucose, hepatocyte growth/scatter factor, keratinocyte growth factor, fibroblast growth factor, epidermal growth factor, insulin-like growth factor, nicotinamide, or autocrine growth factors produced by IPSCs.

7. The method of claim 6 in which the glucose concentration in the re-fed medium is about 16.7 mM.

8. The method, according to claim 1, wherein differentiation of cultured stem cells is initiated at about 4 to 5 weeks of culture growth by re-feeding of said pancreatic cell culture with the nutrient medium supplemented with homologous normal serum.

9. The method, according to claim 1, wherein after cell differentiation is initiated by re-feeding the culture, the culture is re-fed at about one-week intervals.

10. The method, according to claim 1, wherein the normal serum is obtained from the same mammalian species from which the islet cells were obtained.

11. The method, according to claim 1, wherein ar islet-like tissue structure is produced after differentiation of said IPSCs.

12. A method for producing an endocrine hormone which comprises culturing pancreatic cells according to claim 1, and recovering said endocrine hormone from said pancreatic cell culture.

13. The method, according to claim 12, wherein said hormone is a human hormone.

14. The method, according to claim 12, wherein said hormone is a mouse hormone.

15. The method, according to claim 12, wherein differentiation is initiated at about 4 to 5 weeks of culture growth by re-feeding of said IPSC cell culture with said nutrient medium supplemented with normal serum.

16. The method, according to claim 12, wherein said endocrine hormone is selected from the group consisting of insulin, glucagon and somatostatin.

17. The method, according to claim 1, wherein the islet-like structure comprises cells selected from the group consisting of $\alpha$ cells, $\beta$ cells and $\delta$ cells.

18. A method for in vitro neogenesis of islet-like structures from pluripotent stem or progenitor cells which comprises:

a. establishing a stromal, or "nurse", cell monolayer of ductal pancreatic epithelial cells which permits the generation of IPSCs;

b. inducing stem/progenitor cell proliferation with culture conditions which promote cyclical regeneration of IPSCs and also prevent premature differentiation of the IPSC; and c. expanding and differentiating the IPSCs to produce an islet-like structure comprising $\alpha$, $\beta$, and $\delta$ cells.

19. The method of in vitro neogenesis of islets according to claim 18 which comprises:

a dispersing and leaving undisturbed pancreatic cells in a minimal culture medium comprising little or no glucose, serum at a concentration below about 0.5%, essential amino acids for the cells of the species from which the pancreatic cells were obtained, and a rudimentary lipid source, until about 99% of the cells in said culture have died (phase I);

b. re-feeding the culture of step (a) with said minimal medium supplemented with about 1–10 mM glucose and about 0.5%–10% serum (but less than a toxic amount of said serum) and re-feeding about once a week until rapid proliferation occurs;

c. re-feeding the culture of step (b) with said minimal medium supplemented with said 0.5%–1 0% serum and about 10–25 mM glucose and, optimally, added growth or cellular factors (phase III);

d. allowing islet-like structures to bud into the medium; and e. recovering said islet-like structures.

* * * * *

UNITED STATES PATENT AND TRADEMARK OFFICE
CERTIFICATE OF CORRECTION

PATENT NO. : 6,001,647
DATED : December 14, 1999
INVENTOR(S) : Ammon B. Peck, et al.

It is certified that error appears in the above-identified patent and that said Letters Patent is hereby corrected as shown below:

On the title page, item [73] Assignee, should read:

--University of Florida
Research Foundation, Inc.
Gainesville, FL--.

Signed and Sealed this

Twelfth Day of June, 2001

*Attest:*

*Attesting Officer*

NICHOLAS P. GODICI
*Acting Director of the United States Patent and Trademark Office*